United States Patent
Dodd

(10) Patent No.: US 10,106,552 B2
(45) Date of Patent: Oct. 23, 2018

(54) COMPOUNDS INHIBITING EUKARYOTIC ELONGATION FACTOR 2 KINASE ACTIVITY

(71) Applicant: Longevica Pharmaceuticals, Inc., Princeton, NJ (US)

(72) Inventor: John H. Dodd, Spring Mills, PA (US)

(73) Assignee: Longevica Pharmaceuticals, Inc., Princeton, NJ (US)

( * ) Notice: Subject to any disclaimer, the term of this patent is extended or adjusted under 35 U.S.C. 154(b) by 0 days.

(21) Appl. No.: 15/152,941

(22) Filed: May 12, 2016

(65) Prior Publication Data

US 2016/0318948 A1 Nov. 3, 2016

Related U.S. Application Data

(63) Continuation of application No. PCT/US2014/065183, filed on Nov. 12, 2014.

(60) Provisional application No. 61/903,539, filed on Nov. 13, 2013.

(51) Int. Cl.

| C07D 495/04 | (2006.01) |
|---|---|
| A61K 31/4365 | (2006.01) |
| C07D 495/10 | (2006.01) |
| A61K 45/06 | (2006.01) |
| A61K 31/704 | (2006.01) |
| A61K 31/4743 | (2006.01) |
| A61K 31/4747 | (2006.01) |

(52) U.S. Cl.
CPC ........ *C07D 495/04* (2013.01); *A61K 31/4365* (2013.01); *A61K 31/4743* (2013.01); *A61K 31/4747* (2013.01); *A61K 31/704* (2013.01); *A61K 45/06* (2013.01); *C07D 495/10* (2013.01)

(58) Field of Classification Search
CPC ........... C07D 495/04; C07D 475/10; A61K 31/4365; A61K 31/4743
USPC ............................................ 546/80
See application file for complete search history.

(56) References Cited

U.S. PATENT DOCUMENTS 7,465,742 B2 * 12/2008 Chen ............... C07D 495/04
514/232.8

OTHER PUBLICATIONS

Caplus English abstract Shestopalov et al DN 106:196288 (Year: 1986).*
Eukaryotic Elongation Factor 2 Kinase (eEF2K) in cancer. Xuemin Wang et al. (Year: 2017).*

* cited by examiner

*Primary Examiner* — Rita J Desai
(74) *Attorney, Agent, or Firm* — Stephen A. Slusher

(57) ABSTRACT

Eukaryotic elongation factor 2 kinase inhibitors of the formula

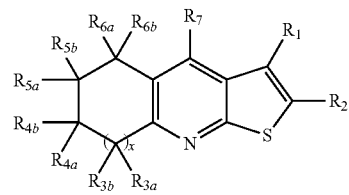

where $R_1$, $R_2$, $R_{3a}$, $R_{3b}$, $R_{4a}$, $R_{4b}$, $R_{5a}$, $R_{5b}$, $R_{6a}$, $R_{6b}$, $R_7$ and x are as defined in the specification, pharmaceutical compositions and formulations including compounds of the foregoing formula, and methods of preventing, ameliorating or treating indications, conditions, disorders or syndromes associated with elongation factor 2 phosphorylation.

11 Claims, 3 Drawing Sheets

COMPOUNDS INHIBITING EUKARYOTIC ELONGATION FACTOR 2 KINASE ACTIVITY

CROSS-REFERENCE TO RELATED APPLICATIONS

This application is a continuation application of International Application No. PCT/US2014/065183, published as International Publication No. WO 2014/102752 A1, entitled "Compounds Inhibiting Eukaryotic Elongation Factor 2 Kinase Activity", filed on Nov. 12, 2014, which in turn claims priority to and the benefit of the filing of U.S. Provisional Patent Application Ser. No. 61/903,539, entitled "Compounds Inhibiting Eukaryotic Elongation Factor 2 Kinase Activity", filed Nov. 13, 2013, and the specification and claims of each of the foregoing are incorporated herein by reference.

BACKGROUND OF THE INVENTION

Technical Field

The present invention relates to compounds for inhibiting the enzyme eukaryotic elongation factor 2 kinase and use thereof in medical therapies and applications.

Background Art

The listing or discussion of a prior-published document in this specification should not necessarily be taken as an acknowledgement that the document is part of the state of the art or is common general knowledge.

Eukaryotic elongation factor 2 kinase (eEF2K) is an ubiquitous, evolutionarily-conserved protein kinase that phosphorylates its only known target, elongation factor 2 (EF2), resulting in arrest of protein translation. (Ryazanov A G, Shestakova E A, Natapov P G. Phosphorylation of elongation factor 2 by EF-2 kinase affects rate of translation. *Nature* 1988, 334(6178):170-3; Sivan G, Kedersha N, Elroy-Stein O. Ribosomal slowdown mediates translational arrest during cellular division. *Mol. Cel. Biol.* 2007, 27(19):6639-46.) EF2 promotes ribosomal translocation, the reaction that results in the movement of the ribosome along mRNA during translation. Phosphorylation of EF2 arrests translation, such that this is a critical mechanism by which the rate of protein synthesis is regulated. (Ryazanov A G. Ca2+/calmodulin-dependent phosphorylation of elongation factor 2. *FEBS Lett.* 1987, 214:331-3).

Inhibition of eEF2K is of potential utility in treating a number of diseases and conditions, including various types of cancer and radiation injury, and as an adjunct to chemotherapy and similar agents to limit apoptosis of normal cells. Thus one application is as a radioprotective agent, limiting radiation-induced apoptosis with natural radiation, unintentional exposure to radiation and radiation therapy. Another application is to mitigate side effects associated with drug and radiation therapy.

eEF2K inhibitors are known and described in the prior art. (Lockman J W, Reeder M D, Suzuki K, Ostanin K, Hoff R, Bhoite L, et al. Inhibition of eEF2-K by thieno[2,3-b]pyridine analogues. *Bioorg. Med. Chem. Lett.* 2010, 20(7): 2283-6; Chen Z, Gopalakrishnan S M, Bui M-H, Soni N B, Warrior U, Johnson E F, et al. 1-Benzyl-3-cetyl-2-methylimidazolium iodide (NH125) induces phosphorylation of eukaryotic elongation factor-2 (eEF2): a cautionary note on the anticancer mechanism of an eEF2 kinase inhibitor. *J. Biol. Chem.* 2011, 286(51):43951-8; and Cho S I, Koketsu M, Ishihara H, Matsushita M, Nairn A C, Fukazawa H, et al. Novel compounds, "1,3-selenazine derivatives" as specific inhibitors of eukaryotic elongation factor-2 kinase. *Biochim Biophys Acta* 2000, 1475(3):207-15.) However, no eEF2K inhibitor has been developed that is suitable for use as a drug.

There is a significant and substantial need for agents which inhibit eEF2K and which limit or inhibit the phosphorylation of EF2, which agents have properties that are suitable for use as pharmaceutical agents. The present invention addresses this by providing eEF2K inhibitors which may be used as drugs for the treatment or prophylaxis of a variety of diseases and conditions. It is against this background that the present invention as made.

SUMMARY OF THE INVENTION

In one embodiment, the invention provides a compound of formula I:

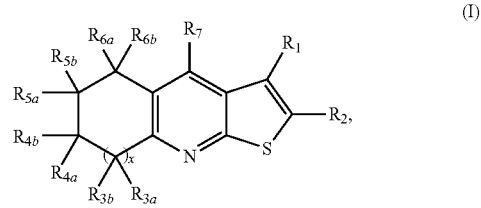

(I)

wherein:
$R_1$ is —$N(R_8)_2$;
$R_2$ is —$C(=O)$—$N(R_8)_2$;
$R_{3a}$ and $R_{3b}$, if X is 1, are
each H, or
each independently $C_{1-3}$ linear or branched alkyl, optionally together forming cycloalkyl, or
one of $R_{3a}$ or $R_{3b}$ is $C_{1-3}$ linear or branched alkyl and the other is H, or
one of $R_{3a}$ or $R_{3b}$ is aryl and the other is H, or
one of $R_{3a}$ or $R_{3b}$ is H and the other is $C_{1-3}$ linear alkyl forming a cycloalkyl through
one of $R_{5a}$, $R_{5b}$, $R_{6a}$ or $R_{6b}$, or
$R_{3a}$ and $R_{3b}$ together are (=CH)—$R_9$;
$R_{4a}$ and $R_{4b}$ are
each H, or
each independently $C_{1-3}$ linear or branched alkyl, optionally together forming cycloalkyl, or
one of $R_{4a}$ or $R_{4b}$ is $C_{1-3}$ linear or branched alkyl and the other is H, or
one of $R_{4a}$ or $R_{4b}$ is aryl and the other is H, or
one of $R_{4a}$ or $R_{4b}$ is H and the other is $C_{1-3}$ linear alkyl forming a cycloalkyl through
one of $R_{6a}$ or $R_{6b}$, or
if x is 0, $R_{4a}$ and $R_{4b}$ together are (=CH)—$R_9$;
$R_{5a}$ and $R_{5b}$ are
each H, or
each independently $C_{1-3}$ linear or branched alkyl, optionally together forming cycloalkyl, or
one of $R_{5a}$ or $R_{5b}$ is $C_{1-3}$ linear or branched alkyl and the other is H, or
one of $R_{5a}$ or $R_{5b}$ is aryl and the other is H, or
if x is 1, one of $R_{5a}$ or $R_{5b}$ forms a cycloalkyl with $R_{3a}$ or $R_{3b}$ and the other is H;
$R_{6a}$ and $R_{6b}$ are
each H, or
each independently $C_{1-3}$ linear or branched alkyl, optionally together forming cycloalkyl, or one of $R_{6a}$ or $R_{6b}$ is $C_{1-3}$ linear or branched alkyl and the other is H, or one of $R_{6a}$ or $R_{6b}$ is aryl and the other is H, or one of $R_{6a}$ or $R_{6b}$ forms a cycloalkyl with one of $R_{3a}$ or $R_{3b}$ if X is 1, or if x is 0 or 1, with $R_{4a}$ or $R_{4b}$, and the other is H;

on the proviso that each member of at least one of the pairs $R_{3a}$ and $R_{3b}$, $R_{4a}$ and $R_{4b}$, $R_{5a}$ and $R_{5b}$, or $R_{6a}$ and $R_{6b}$ is independently $C_{1-3}$ linear or branched alkyl, optionally together forming cycloalkyl, or alternatively at least one of $R_{3a}$, $R_{3b}$, $R_{4a}$, $R_{4b}$, $R_{5a}$, $R_{5b}$, $R_{6a}$ and $R_{6b}$ is aryl, or alternatively if x is 1 then one of $R_{3a}$ or $R_{3b}$ is a $C_{1-3}$ linear alkyl forming a cycloalkyl with one of $R_{5a}$, $R_{5b}$, $R_{6a}$ or $R_{6b}$ or one of $R_{4a}$ or $R_{4b}$ is a $C_{1-3}$ linear alkyl forming a cycloalkyl with one $R_{6a}$ or $R_{6b}$, or alternatively if x is 1 then $R_{3a}$ and $R_{3b}$ together are (=CH)—$R_9$, or alternatively if x is 0 then one of $R_{4a}$ or $R_{4b}$ is a $C_{1-3}$ linear alkyl forming a cycloalkyl with one $R_{6a}$ or $R_{6b}$, or alternatively if x is 0 then $R_{4a}$ and $R_{4b}$ together are (=CH)—$R_9$;

$R_7$ is a 3- to 6-membered saturated or unsaturated carbocyclic ring or a heterocyclic ring containing 1 to 3 heteroatoms independently selected from N, O and S, such carbocyclic or heterocyclic ring optionally substituted with one or two ring substituents selected from the group consisting of halogen and $C_1$ to $C_4$ linear, branched or cyclic alkyl, or $R_7$ is a $C_1$ to $C_6$ linear, branched or cyclic alkyl;

$R_8$ in each instance is independently H or a $C_1$ to $C_4$ linear, branched or cyclic alkyl chain;

$R_9$ is a 3- to 6-membered saturated or unsaturated carbocyclic ring or heterocyclic ring containing 1 to 3 heteroatoms independently selected from N, O and S, optionally substituted with one or two ring substituents selected from the group consisting of halogen and $C_1$ to $C_4$ linear, branched or cyclic alkyl; and x is 0 or 1.

The invention further provides pharmaceutical compositions comprising a compound of formula I and a pharmaceutically acceptable carrier. Such pharmaceutical compositions may be employed in a method for limiting EF2 phosphorylation in a human or non-human mammal, the method comprising the step of administering the pharmaceutical composition. Such pharmaceutical composition may further be employed in a method for treating a condition responsive to limiting EF2 phosphorylation in a human or non-human mammal, comprising the step of administering the pharmaceutical composition to the human or non-human mammal in a pharmaceutically effective amount.

The invention further includes methods and compounds for altering a disorder or condition associated with EF2 phosphorylation, including associated with disadvantageous cellular apoptosis, comprising administering to a patient a pharmaceutically effective amount of a compound of the present invention.

In one embodiment the disorder or condition is a cancer, including but not limited to a brain cancer or breast cancer.

In another embodiment the disorder or condition is Alzheimer's or other neurodegenerative disease, wherein the compounds and methods of the present invention inhibit the deposit of amyloid plaques in the brain of a patient with Alzheimer's or other neurodegenerative disease or with risk factors for Alzheimer's or other neurodegenerative disease.

In another embodiment the methods and compounds of the present invention limit or prevent injury to normal cells and tissues resulting from administration of chemotherapeutic agents. The chemotherapeutic agent may be doxorubicin.

In another embodiment the methods and compounds of the present invention sensitize tumor cells to treatment, such treatment including, but not limited to, use of therapeutic agents, including chemotherapeutic agents or radiation therapy, and nutrient deprivation. If a chemotherapeutic agent is employed, the chemotherapeutic agent may be doxorubicin.

In another embodiment the methods and compounds of the present invention may be used to protect heart or neural tissue, including brain tissue, from injury or degradation during ischemic injury, hypoxia, stroke or similar physical insult.

In another embodiment the methods and compounds of the present invention may be used to protect liver cells or limit or minimize damage to liver cells during or resulting from hetapotoxicity, such as chemical-driven liver damage, or viral or other infectious disease, such as hepatitis C.

In another embodiment the methods and compounds of the present invention may be used where the disorder or condition is injury to normal cells and tissues resulting from radiation, including radiation therapy for treatment of other diseases, such as cancers, and accidental, industrial or military-related exposure to radiation.

In another embodiment the methods and compounds of the present invention are used as a prophylactic or preventative, such as limiting injury to normal cells and tissues in subjects at risk of exposure to medical, industrial or military-related radiation.

In another embodiment the methods and compounds of the present invention are used as a prophylactic or preventative, such as limiting injury to normal cells and tissues in subjects at risk of exposure to toxins, including without limit hetapotoxins.

In yet another embodiment the methods and compounds of the present invention are used to treat major depressive disorders, either singly or in combination with one or more antidepressant medications.

Other objects, advantages and novel features, and the further scope of applicability of the present invention will be set forth in part in the detailed description to follow, and in part will become apparent to those skilled in the art upon examination of the following, or may be learned by practice of the invention.

BRIEF DESCRIPTION OF THE DRAWINGS

The accompanying drawings, which are incorporated into and form a part of the specification, illustrate one or more embodiments of the present invention and, together with the description, serves to explain the principles of the invention. The drawings are only for the purpose of illustrating one or more preferred embodiments of the invention and are not to be construed as limiting the invention.

DETAILED DESCRIPTION OF THE INVENTION

1. Compounds of the Invention

Figure 1:
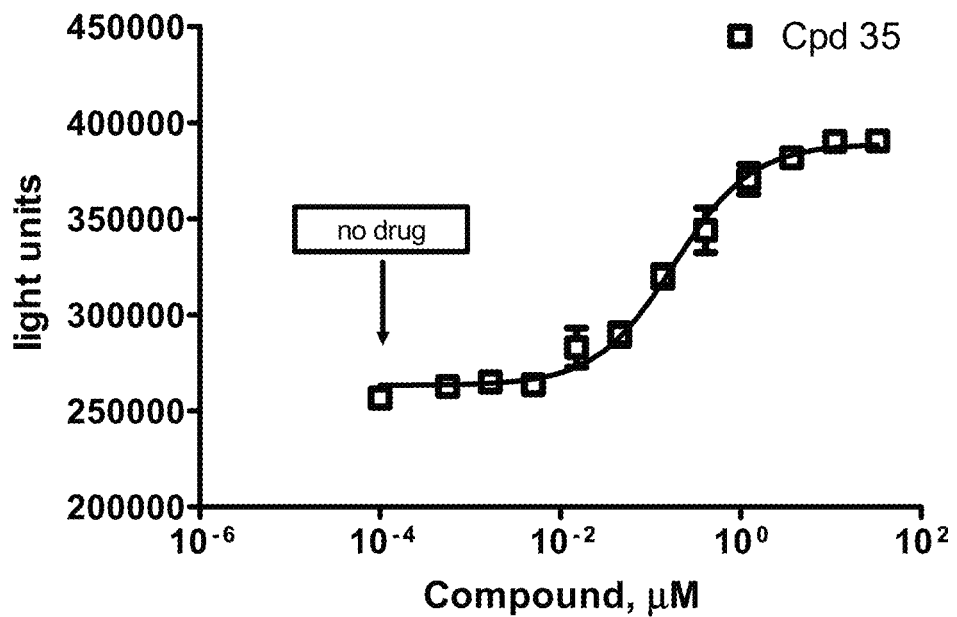
FIG. 1 is a dose-response plot for Compound 35, utilized to calculate $IC_{50}$ values. Compound 35 was added as 0.5 µL of a 100% DMSO solution, with values expressed in µM $IC_{50}$ values.

The invention relates to compounds of formula I as described above.

Compounds of the invention are useful for treating conditions in human or non-human mammals responsive to inhibition of eEF2K. In one aspect, such conditions are treated by administering a pharmaceutical composition comprising the compound of formula I and a pharmaceutically acceptable carrier, preferably by administering a pharmaceutically effective amount of such pharmaceutical composition.

Compounds of the invention are further useful for treating a disease in a human or non-human mammal responsive to limiting EF2 phosphorylation. In one aspect, such conditions are treated by administering a pharmaceutical composition comprising the compound of formula I and a pharmaceutically acceptable carrier, preferably by administering a pharmaceutically effective amount of such pharmaceutical composition.

For certain diseases, including but not limited to cancers, the pharmaceutical composition comprising a compound of formula I may be administered in combination with administration of a chemotherapeutic agent. The chemotherapeutic agent may be administered prior to, in conjunction with or after administering the pharmaceutical composition comprising the compound of formula (I). In one aspect, the chemotherapeutic agent is an anthracycline such as doxorubicin.

For certain diseases, including but not limited to cancers, the pharmaceutical composition comprising a compound of formula I may be administered in conjunction with administering radiation therapy. The radiation therapy may be administered prior to, in conjunction with or after administering the pharmaceutical composition comprising the compound of formula (I).

In certain embodiments, the compounds of formula I are those in which:

(1) each member of one of the pairs $R_{3a}$ and $R_{3b}$, $R_{4a}$ and $R_{4b}$, $R_{5a}$ and $R_{5b}$, and $R_{6a}$ and $R_{6b}$ is independently $C_{1-3}$ linear or branched alkyl, optionally together forming cycloalkyl, and each member of the remaining pairs $R_{3a}$ and $R_{3b}$, $R_{4a}$ and $R_{4b}$, $R_{5a}$ and $R_{5b}$, and $R_{6a}$ and $R_{6b}$ are H;

(2) each member of one of the pairs $R_{5a}$ and $R_{5b}$, and $R_{6a}$ and $R_{6b}$ or, if X is 1, $R_{4a}$ and $R_{4b}$, is independently $C_{1-3}$ linear or branched alkyl, optionally together forming cycloalkyl, if x is 1 then $R_{3a}$ and $R_{3b}$ together are (=CH)—$R_9$ and if x is 0 then $R_{4a}$ and $R_{4b}$ together are (=CH)—$R_9$, and each member of the remaining pairs $R_{3a}$ and $R_{3b}$, $R_{4a}$ and $R_{4b}$, $R_{5a}$ and $R_{5b}$, and $R_{6a}$ and $R_{6b}$ are H;

(3) each member of one of the pairs $R_{3a}$ and $R_{3b}$, $R_{4a}$ and $R_{4b}$, $R_{5a}$ and $R_{5b}$, and $R_{6a}$ and $R_{6b}$ is independently $C_{1-3}$ linear or branched alkyl, optionally together forming cycloalkyl, one of the remaining pairs $R_{3a}$ and $R_{3b}$, $R_{4a}$ and $R_{4b}$, $R_{5a}$ and $R_{5b}$, and $R_{6a}$ and $R_{6b}$ contains a member that is H and a member that is $C_{1-3}$ linear or branched alkyl, and each member of the remaining pairs $R_{3a}$ and $R_{3b}$, $R_{4a}$ and $R_{4b}$, $R_{5a}$ and $R_{5b}$, and $R_{6a}$ and $R_{6b}$ are H;

(4) $R_7$ and $R_9$ are each independently phenyl, furanyl, thiophenyl, thiozolyl, pyrrolyl or cyclopropyl, optionally substituted with one or two ring substituents selected from the group consisting of halogen and $C_1$ to $C_4$ linear, branched or cyclic alkyl;

(5) the compound is of the formula

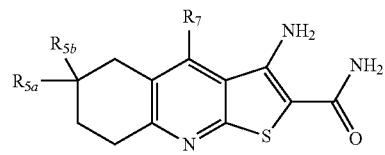

wherein each of $R_{5a}$ and $R_{5b}$ is independently $C_{1-3}$ linear or branched alkyl, optionally together forming cycloalkyl;

(6) the compound is of the formula

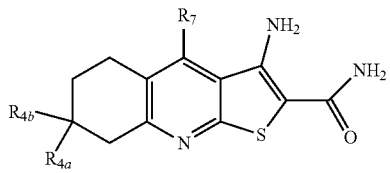

wherein each of $R_{4a}$ and $R_{4b}$ is independently $C_{1-3}$ linear or branched alkyl, optionally together forming cycloalkyl;

(7) the compound is of the formula

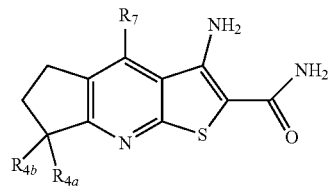

wherein each of $R_{4a}$ and $R_{4b}$ is independently $C_{1-3}$ linear or branched alkyl, optionally together forming cycloalkyl;

(8) the compound is of the formula

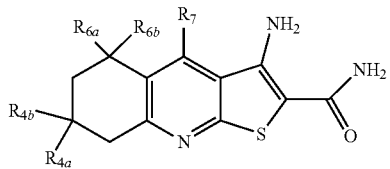

wherein each of $R_{4a}$ and $R_{4b}$ is independently $C_{1-3}$ linear or branched alkyl, optionally together forming cycloalkyl, and one of $R_{6a}$ or $R_{6b}$ is $C_{1-3}$ linear or branched alkyl and the other is H;

(9) the compound is of the formula

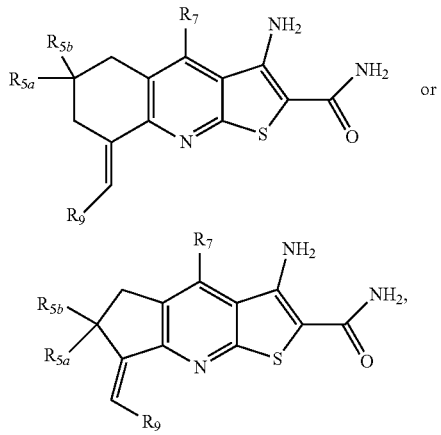

wherein each of $R_{5a}$ and $R_{5b}$ is independently $C_{1-3}$ linear or branched alkyl, optionally together forming cycloalkyl;

(10) the compound is of the formula

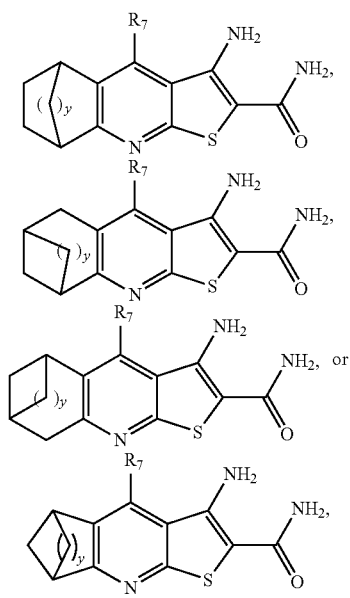

wherein y is 1 to 3;
(11) aryl is phenyl;
(12) one of $R_{3a}$, $R_{3b}$, $R_{4a}$, $R_{4b}$, $R_{5a}$, $R_{5b}$, $R_{6a}$ and $R_{6b}$ is aryl and the remaining of $R_{3a}$, $R_{3b}$, $R_{4a}$, $R_{4b}$, $R_{5a}$, $R_{5b}$, $R_{6a}$ and $R_{6b}$ are H;
(13) if x is 1 then $R_{3a}$ and $R_{3b}$ together are (=CH)—$R_9$ and if x is 0 then $R_{4a}$ and $R_{4b}$ together are (=CH)—$R_9$, and one member of one of the pairs $R_{4a}$ and $R_{4b}$, but only if x is 1, or $R_{5a}$ and $R_{5b}$, or $R_{6a}$ and $R_{6b}$ is aryl and the remaining of $R_{4a}$, $R_{4b}$, $R_{5a}$, $R_{5b}$, $R_{6a}$ and $R_{6b}$ are H;
(14) $R_7$ is phenyl, furanyl, thiophenyl, thiozolyl, pyrrolyl or cyclopropyl, optionally substituted with one or two ring substituents selected from the group consisting of halogen and $C_1$ to $C_4$ linear, branched or cyclic alkyl; and

(15) the compound is of the formula

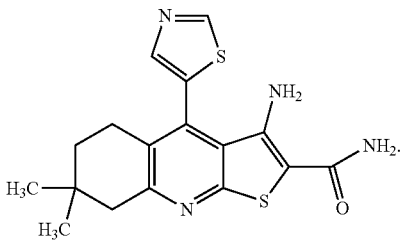 [SMILES: CC1(C)CCc2c(nc3sc(C(N)=O)c(N)c3c2-c2cncs2)C1]

Representative compounds of the embodiment (1) above include compound numbers 2, 6, 7, 8, 10, 11, 12, 17, 18, 19, 20 21, 23, 24, 25, 26, 27, 28, 29, 30, 31, 32, 33, 34, 35, 37, 38, 39, 40, 41 and 42.

Representative compounds of the embodiment (2) above include compound numbers 1, 14 and 22.

Representative compounds of the embodiment (3) above include compound number 36.

Representative compounds of the embodiment (4) above include compound numbers 1, 3, 5, 14 and 22.

Representative compounds of the embodiment (5) above include compound numbers 2, 6, 20 and 33.

Representative compounds of the embodiment (6) above include compound numbers 7, 10, 11 and 35.

Representative compounds of the embodiment (7) above include compound numbers 9, 15, 17, 18, 19, 23, 24, 25, 26, 27, 28, 29, 30, 31, 32, 34 and 40.

Representative compounds of the embodiment (8) above include compound numbers 12, 26 and 36.

Representative compounds of the embodiment (9) above include compound numbers 1, 14 and 22.

Representative compounds of the embodiment (10) above include compound number 43.

Representative compounds of the embodiment (11) above include compound numbers 3, 4 and 13.

Representative compounds of the embodiment (12) above include compound numbers 4 and 13.

Representative compounds of the embodiment (13) above include compound number 3.

The compounds of formula I are further characterized in that:
each member of at least one of the pairs $R_{3a}$ and $R_{3b}$, $R_{4a}$ and $R_{4b}$, $R_{5a}$ and $R_{5b}$, or $R_{6a}$ and $R_{6b}$ is independently $C_{1-3}$ linear or branched alkyl, optionally together forming cycloalkyl, for example such that each of $R_{4a}$ and $R_{4b}$ are methyl or each of $R_{5a}$ and $R_{5b}$ are methyl, or as with compound number 42, where $R_{3a}$ and $R_{3b}$ are each alkyl together forming cycloalkyl;
or alternatively at least one of $R_{3a}$, $R_{3b}$, $R_{4a}$, $R_{4b}$, $R_{5a}$, $R_{5b}$, $R_{6a}$ and $R_{6b}$ is aryl, as for example with compound numbers 4 and 13;
or alternatively if x is 1 then one of $R_{3a}$ or $R_{3b}$ is a $C_{1-3}$ linear alkyl forming a cycloalkyl with one of $R_{5a}$, $R_{5b}$, $R_{6a}$ or $R_{6b}$ or one of $R_{4a}$ or $R_{4b}$ is a $C_{1-3}$ linear alkyl forming a cycloalkyl with one $R_{6a}$ or $R_{6b}$, as for example with

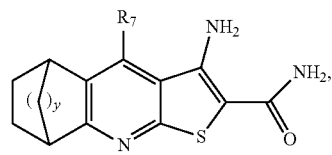

-continued

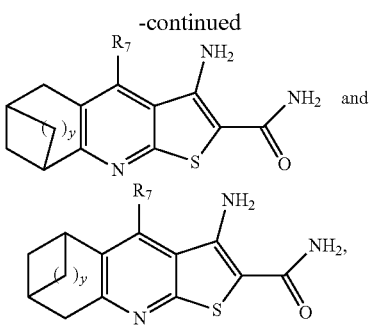

wherein y is 1 to 3;
or alternatively if x is 1 then $R_{3a}$ and $R_{3b}$ together are (=CH)—$R_9$, as in compound numbers 1, 3, 5, 14 and 22;
or alternatively if x is 0 then one of $R_{4a}$ or $R_{4b}$ is a $C_{1-3}$ linear alkyl forming a cycloalkyl with one $R_{6a}$ or $R_{6b}$, as for example with

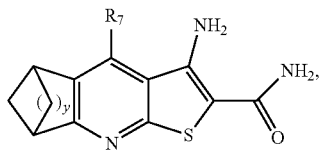

wherein y is 1 to 3;
or alternative if x is 0 then $R_{4a}$ and $R_{4b}$ together are (=CH)—$R_9$, as for example with

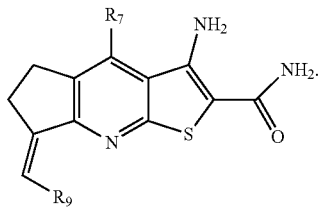

2. Isomeric Purity and Isolation

Certain of the compounds of the invention can contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of the invention, encompass the racemic form of compounds of the invention as well as all enantiomers and stereoisomers, that is, both the stereomerically pure form (e.g., geometrically pure, enantiomerically pure, or diastereomerically pure) and enantiomeric and stereoisomeric mixtures.

A compound of the invention is considered optically active or enantiomerically pure (i.e., substantially the R-form or substantially the S-form) with respect to a chiral center when the compound is about 90% ee (enantiomeric excess) or greater, preferably, equal to or greater than 95% ee with respect to a particular chiral center. A compound of the invention is considered to be in enantiomerically enriched form when the compound has an enantiomeric excess of greater than about 80% ee, preferably greater than about 90% ee. As used herein, a racemic mixture means about 50% of one enantiomer and about 50% of its corresponding enantiomer relative to all chiral centers in the molecule. Thus, the invention encompasses all enantiomerically pure, enantiomerically enriched, and racemic mixtures of compounds of the invention.

Enantiomeric and stereoisomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically- or enantiomerically-pure intermediates, reagents, and catalysts by well known asymmetric synthetic methods.

When administered to a patient, the compounds of the invention are administered in isolated form or as the isolated form in a pharmaceutical composition. As used herein, "isolated" means that the compounds of the invention are separated from other components of either (a) a natural source, such as a plant or cell, preferably bacterial culture, or (b) a synthetic organic chemical reaction mixture. Preferably, the compounds of the invention are purified by conventional techniques. As used herein, "purified" means that when isolated, the isolate contains at least 95%, preferably at least 98%, of a single compound of the invention (or an enantiomeric or diastereomeric mixture thereof) by weight of the isolate.

3. Definitions

"treat", "treating" and "treatment"
The terms "treat," "treating" and "treatment," as used herein, contemplate an action that occurs while a patient is suffering from the specified disease or disorder, which reduces the severity of the disease or disorder.

"pharmaceutically effective amount"
As used herein, the term "pharmaceutically effective amount" means the amount of a compound of the invention that will elicit a biological or medical response in the mammal that is being treated by a medical doctor or other clinician.

"prophylactically effective", "preventing" or "preventive"
As used herein, the term "prophylactically effective" or "preventive" means the amount of a compound of the invention that will prevent or inhibit affliction or mitigate affliction of a mammal with a medical condition that a medical doctor or other clinician is trying to prevent, inhibit, or mitigate before a patient begins to suffer from the specified disease or disorder.

"pharmaceutically acceptable salt(s)"
The term "pharmaceutically acceptable salt(s)", as used herein includes but is not limited to salts of acidic or basic groups that may be present in the compounds of the invention. Compounds that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds of the invention that include an amino moiety also can form pharmaceutically acceptable salts with various amino acids, in addition to the acids mentioned above. Compounds of the invention that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

"alkyl"

As used herein, the term "alkyl" means a saturated, monovalent, unbranched or branched hydrocarbon chain. Examples of alkyl groups include, but are not limited to, $C_{1-6}$ alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl, and longer alkyl groups, such as heptyl and octyl.

"alkenyl"

As used herein, the term "alkenyl" means a monovalent, unbranched or branched hydrocarbon chain having one or more double bonds therein. The double bond of an alkenyl group can be unconjugated or conjugated to another unsaturated group. Suitable alkenyl groups include, but are not limited to $C_{2-6}$ alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene) pentenyl.

"aryl"

As used herein, "aryl" groups of the present invention are $C_{6-14}$ carbocyclic aromatic groups. These aryl groups may comprise one, two or three rings, at least one of which rings must be aromatic. Examples of suitable aryl groups include, but are not limited to, phenyl, anthacenyl, fluorenyl, indenyl, azulenyl and naphthyl as well as part-aromatic, bi- or tri-cyclic moieties such as indanyl or 5,6,7,8-tetrahydronaphthyl. Preferably, an aryl group is a phenyl ring.

"cycloalkyl"

As used herein, the term "cycloalkyl" means a $C_{3-12}$ (e.g. $C_{3-7}$) monocyclic or polycyclic saturated ring comprising carbon and hydrogen atoms and having no carbon-carbon multiple bonds. Examples of cycloalkyl groups include, but are not limited to, $C_{3-7}$ cycloalkyl groups, such as cyclopropyl, cyclobutyl, cyclopentyl, cyclohexyl, and cycloheptyl.

"alkoxy"

As used herein, the term "alkoxy" means an —O-alkyl group, wherein alkyl is as defined above. Preferably, the alkyl chain of an alkyloxy group is from 1 to 6 carbon atoms in length.

"halogen", "halo"

As used herein, the term "halogen" means fluorine, chlorine, bromine, or iodine. Correspondingly, the meaning of the term "halo" encompasses fluoro, chloro, bromo, and iodo.

4. Synthesis of Compounds of the Invention

The compounds of the invention can be obtained via standard, synthetic methodology. Some convenient methods are illustrated in the schemes below. Starting materials useful for preparing the compounds of the invention and intermediates therefor, are commercially available or can be prepared from commercially available materials using known synthetic methods and reagents.

Protecting groups utilized herein denote groups which generally are not found in the final therapeutic compounds but which are intentionally introduced at some stage of the synthesis in order to protect groups which otherwise might be altered in the course of chemical manipulations. Such protecting groups are removed or converted to the desired group at a later stage of the synthesis and compounds bearing such protecting groups thus are of importance primarily as chemical intermediates (although some derivatives also exhibit biological activity). Accordingly, the precise structure of the protecting group is not critical.

Numerous reactions for the formation and removal of such protecting groups are described in a number of standard works including, for example, "Protective Groups in Organic Chemistry", Plenum Press, London and New York, 1973; Greene, Th. W. "Protective Groups in Organic Synthesis", Wiley, New York, 1981; "The Peptides", Vol. I, Schroder and Lubke, Academic Press, London and New York, 1965; "Methoden der organischen Chemie", Houben-Weyl, 4th Edition, Vol. 15/I, Georg Thieme Verlag, Stuttgart 1974; "Protective Groups in Organic Synthesis", 4th Revised edition T. W. Greene & P. G. M. Wutz, Wiley, New York, December 2006, the disclosures of which are incorporated herein by reference.

The following scheme illustrates one methodology for the synthesis of Compound 35 of the Invention, which is 3-Amino-7,7-dimethyl-4-thiazol-5-yl-5,6,7,8-tetrahydrothieno[2,3-b]quinoline-2-carboxylic acid amide. It is understood that this method is generally applicable to the synthesis of the compounds disclosed herein, including the compounds of formula I, and that one of ordinary skill in the art may adapt the general methods disclosed herein for any compound of formula I.

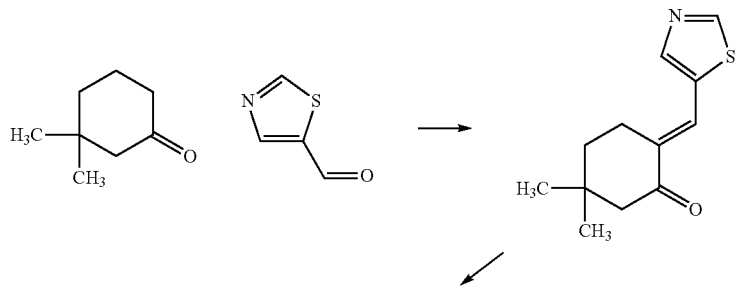

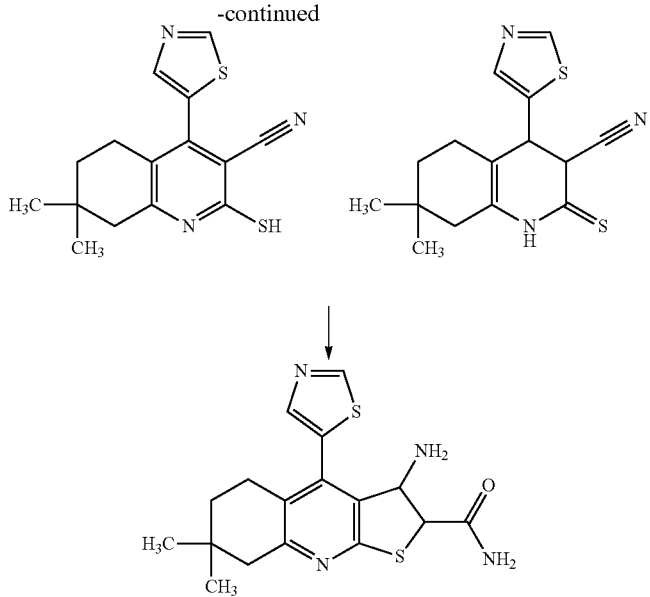

5,5-Dimethyl-2-thiazol-5-yl-methylene-cyclohexanone 3,3-Dimethylcyclohexanone (90%, 0.142 g, 1.02 mmol) was added to a solution of potassium hydroxide (90%, 0.127 g, 2.03 mmol) in methanol (4 mL). A solution of 5-thiazolecarboxaldehyde (0.115 g, 1.02 mmol) in methanol (2 mL) was added dropwise to the reaction solution over 5 minutes. The resultant solution was stirred at ambient temperature for 3 hours. The solution was assayed by LCMS indicating formation of a single product MS: 222.34 (MH$^+$). The solution was used as is in the subsequent reaction.

2-Mercapto-7,7-dimethyl-4-thiazol-5-yl-5,6,7,8-tetrahydroquinoline-3-carbonitrile and 7,7-dimethyl-4-thiazol-5-yl-2-thioxo-1,2,3,4,5,6,7,8-octahydroquinoline-3-carbonitrile 2-Cyanothioacetamide (0.102 g, 1.02 mmol) was added to the solution of 5,5-dimethyl-2-thiazol-5-yl-methylene-cyclohexanone (above), followed by the addition of sodium methoxide (0.165 g, 3.06 mmol). The reaction was protected from light, and heated to reflux for 20 hours, open to the air. The reaction solution was assayed by LCMS indicating the formation of 2 products MS: 302.39 (MH$^+$) and 304.43 (MH$^+$). The resultant solution was used as is in the subsequent step.

3-Amino-7,7-dimethyl-4-thiazol-5-yl-5,6,7,8-tetrahydrothieno[2,3-b]quinoline-2-carboxylic acid amide 2-Bromoacetamide (0.140 g, 1.02 mmol) was added to the solution of 2-mercapto-7,7-dimethyl-4-thiazol-5-yl-5,6,7,8-tetrahydroquinoline-3-carbonitrile and 7,7-dimethyl-4-thiazol-5-yl-2-thioxo-1,2,3,4,5,6,7,8-octahydroquinoline-3-carbonitrile (above), followed by the addition of sodium methoxide (0.055 g, 1.02 mmol). The solution was protected from light, heated at reflux for 21 hours open to the air (note that at 3 hours a precipitate had developed and the reaction was complete by LCMS), then cooled to room temperature, and the solvent was evaporated in vacuo. The residue was suspended in ethyl acetate and water. The product, 0.048 g, was collected by filtration. The organic layer was separated, washed with brine and dried over sodium sulfate. The solvent was evaporated in vacuo, to afford additional crude product, 0.253 g. The combined product was pre-absorbed onto silica gel, applied to a flash chromatography column and eluted with a step gradient of methanol (0% to 8%) in dichloromethane with ammonium hydroxide (0.2%) to afford the product as a yellow solid, 0.154 g (42%). Impure fractions were combined and purified by flash chromatography using a step gradient of ethyl acetate (0% to 90%) in hexanes as the eluent to afford additional product (0.043 g, 12%). MS: 359.63 (MH$^+$); $^1$H NMR (DMSO-d6): δ 9.42 (s, 1H), 8.04 (s, 1H), 7.18 (br s, 2H), 5.75 (br s 2H), 2.77 (s, 2H), 2.4-2.48 (m, 2H), 1.48-1.58 (m, 2H) and 0.98 (s, 6H).

Isolation of the final product may also be accomplished by evaporating the solvent in vacuo, and suspending the residue in water. The product was collected by filtration, washed with water and purified by flash chromatography.

For making other compounds of the invention, 1 equivalent of an aromatic carboxaldehyde in methanol is added dropwise to a solution of 1 equivalent of a cyclic aliphatic ketone and 2 equivalents of potassium hydroxide. The reaction is monitored by LCMS until starting materials are consumed and the product has been formed. One equivalent of 2-cyanothioacetamide is added followed by 3 equivalents of sodium methoxide. The reaction is protected from light and heated at reflux, open to the air. The reaction is monitored by LCMS until starting materials are consumed. One equivalent of 2-bromoacetamide is added followed by 1 equivalent of sodium methoxide. The reaction is protected from light, and heated at reflux open to the air. The reaction is monitored by LCMS, until the starting materials are consumed. The solvent is evaporated in vacuo, and the residue triturated in water. The water is decanted or removed by filtration. The product is dissolved in an organic solvent, treated with a drying agent, pre-absorbed onto silica gel, and isolated by flash chromatography using a gradient of either methanol in dichloromethane with ammonium hydroxide buffer, or a gradient of ethyl acetate in hexanes.

The compounds of the invention also include compounds which are identical to those recited in the structural formulas and claims, but for the fact that one or more atoms depicted in the structural formulas are replaced by an atom having an atomic mass or mass number different from the atomic mass or mass number usually found in nature. Examples of isotopes that can be incorporated into compounds of the invention include isotopes of hydrogen, carbon, nitrogen and oxygen, such as $^{2}H$, $^{3}H$, $^{13}C$, $^{14}C$, $^{15}N$, $^{18}O$ and $^{17}O$, respectively. Compounds of the invention and pharmaceutically acceptable salts or solvates of said compounds which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, may have use in a variety of assays, such as in drug and/or substrate tissue distribution assays. Substitution with heavier isotopes, such as substitution of one or more hydrogen atoms with deuterium ($^{2}H$), can provide pharmacological advantages in some instances, including increased metabolic stability. Isotopically labeled compounds of the structural formulas disclosed herein can generally be prepared by substituting an isotopically labeled reagent for a non-isotopically labeled reagent.

5. Formulations and Administration

The compounds may be formulated by any means known in the art, including but not limited to tablets, capsules, caplets, suspensions, powders, lyophilized forms, gels, ophthalmic preparations and aerosols and may be mixed and formulated with buffers, binders, stabilizers, anti-oxidants and other agents known in the art. The compounds may be administered by any systemic, partially systemic or local means known in the art, including but not limited to intravenous injection, intramuscular injection, subcutaneous injection, administration through mucous membranes, oral administration, dermal administration, skin patches, aerosols, ocular, creams, gels and the like.

The invention further provides a pharmaceutical composition that includes a compound of this invention and a pharmaceutically acceptable carrier. The compound of this invention may thus be formulated or compounded into pharmaceutical compositions that include at least one compound of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, mannitol, sodium chloride or sodium citrate. For injection or other liquid administration formulations, water containing at least one or more buffering constituents is suitable for certain compounds of this invention, and one or more pharmaceutically acceptable oils, optionally containing one or more buffering constituents, are suitable for other compounds of this invention. Such injection or other liquid administration formulations may further include stabilizing agents, preservatives and solubilizing agents. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed.

When formulated with a pharmaceutically acceptable carrier, the compound of this invention may be present in the pharmaceutical composition in a concentration from 0.1 to 99.5% (such as from 0.5 to 95%) by weight of the total mixture. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, such that the dosage may be formulated so as to effect delivery of a compound of this invention over a period of time.

The compounds of this invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

The compounds and pharmaceutical compositions of this invention may be administered by injection, which injection may be intravenous, subcutaneous, intramuscular, intraperitoneal or by any other means known in the art. In general, any route of administration by which the compounds of this invention are introduced across an epidermal layer of cells may be employed. Administration means may include administration through mucous membranes, buccal administration, oral administration, dermal administration, inhalation administration, nasal administration and the like. The dosage for treatment is administration, by any of the foregoing means or any other means known in the art, of an amount sufficient to bring about the desired therapeutic effect.

Certain of the compounds of this invention are poorly soluble in water, and may precipitate or fall out of solution in formulations containing more than about ten percent, or about twenty percent, or about thirty percent water. Thus injectable pharmaceutical compositions may be oleaginous suspensions formulated according to the known art using suitable dispersing or wetting agents and suspending agents, as required or desired. Fixed oils may be conventionally employed as a solvent or suspending medium. Any pharmaceutically acceptable oil customarily used for injection purposes, whether vegetable, synthetic or semi-synthetic oil, may be employed. In one aspect liquid fatty acid esters that contain as the acid component a long-chained fatty acid having from 8-22 carbon atoms, especially from 12-22 carbon atoms, may be employed, such as lauric acid, tridecylic acid, myristic acid, pentadecylic acid, palmitic acid, margaric acid, stearic acid, arachidic acid, behenic acid or corresponding unsaturated acids, e.g., oleic acid, elaidic acid, erucic acid, brasidic acid or linoleic acid, if desired with the addition of antioxidants, e.g., vitamin E, beta-carotene or 3,5-di-tert-butyl-4-hydroxytoluene. The alcohol component of those fatty acid esters has a maximum of 6 carbon atoms and is a mono- or poly-hydroxy, e.g., a mono-, di- or tri-hydroxy; alcohol, e.g., methanol, ethanol, propanol, butanol or pentanol; or the isomers thereof, but especially glycol and glycerol. Thus fatty acid esters such as ethyl oleate, isopropyl myristate, isopropyl palmitate, polyoxyethylene glycerol trioleate, triglycerides of saturated fatty acids with a chain length of $C_8$-$C_{12}$, and especially vegetable oils, such as cottonseed oil, almond oil, olive oil, castor oil, sesame oil, corn germ oil, sesame oil, soybean oil and more especially groundnut or peanut oil, may be employed.

Fatty acids such as oleic acid may be employed in the formulation of injectable pharmaceutical compositions. Alternatively, the compounds of this invention may be dissolved in polyethylene glycol, propylene glycol, ethanol, corn oil, peanut oil, castor oil, cottonseed oil, sesame oil, tragacanth gum, benzyl alcohol, and optionally various buffers known in the art. The carrier or diluent may include time delay constituents, such as glyceryl monostearate or glyceryl distearate alone or with a wax, or other materials well known in the art.

In one aspect, an injectable pharmaceutical composition may comprise dimethyl sulfoxide (DMSO), castor oil and ethanol, such as about 20% DMSO, 45% castor oil and 35% ethanol.

The pharmaceutical composition can be in a solid, semi-solid, or liquid form. For a solid form, the compound and other components may be mixed together by blending, tumble mixing, freeze-drying, solvent evaporation, co-grinding, spray-drying, and other techniques known in the art. A semi-solid pharmaceutical composition suitable for intranasal administration can take the form of an aqueous or oil-based gel or ointment. For example, the compound and other components can be mixed with microspheres of starch, gelatin, collagen, dextran, polylactide, polyglycolide or other similar materials that form hydrophilic gels. In one embodiment the microspheres can be internally loaded or coated with compound of this invention, and upon administration form a gel that adheres to the nasal mucosa. In another embodiment, the formulation is liquid, it being understood that this includes an aqueous solution, an aqueous suspension, an oil solution, an oil suspension, or an emulsion, depending on the physicochemical properties of the compound and other components.

For liquid formulations, excipients necessary or desirable for formulation, stability, and/or bioavailability are included in the pharmaceutical composition. Exemplary excipients include sugars (such as glucose, sorbitol, mannitol, or sucrose), uptake enhancers (such as chitosan), thickening agents and stability enhancers (such as celluloses, polyvinyl pyrrolidone, starch, and the like), buffers, preservatives, and/or acids and bases to adjust the pH. In one embodiment, an absorption promoting component is included in the pharmaceutical composition. Exemplary absorption promoting components include surfactant acids, such as cholic acid, glycocholic acid, taurocholic acid, and other cholic acid derivatives, chitosan and cyclodextrins.

The pharmaceutical composition may further include optional components, such as preservatives and the like. Preservatives may be employed, to prevent or limit bacteria and other microbial growth. One such preservative that may be employed is benzalkonium chloride, such as 0.05% benzalkonium chloride. Other preservatives include benzyl alcohol, methylparaben, propylparaben, butylparaben, chlorobutanol, phenethyl alcohol, phenyl mercuric acetate and the like.

The pharmaceutical composition may also include rheology modifying agents, such as for varying the viscosity of the pharmaceutical composition. Exemplary rheology modify agents include polymers and similar materials, such as sodium carboxymethyl cellulose, algin, carageenans, carbomers, galactomannans, hydroxypropyl methylcellulose, hydroxypropyl cellulose, polyethylene glycols, polyvinyl alcohol, polyvinylpyrrolidone, sodium carboxymethyl chitin, sodium carboxymethyl dextran, sodium carboxymethyl starch, xanthan gum and combinations of the foregoing.

In one aspect, the individual dosage form, such as a tablet or capsule, optionally further includes common pharmaceutical binders such as povidone, diluents, glidants, fillers such as microcrystalline cellulose, lubricants such as magnesium stearate, disintegrants such as croscarmellose sodium, preservatives, colorants and the like in their usual known sizes and amounts.

Depending on the formulation and route of administration, if in an aqueous solution compounds and pharmaceutical compositions of this invention are appropriately buffered by means of saline, acetate, phosphate, citrate, acetate or other buffering agents, which are at any physiologically acceptable pH, generally from about pH 4 to about pH 8. A combination of buffering agents may also be employed, such as phosphate buffered saline, a saline and acetate buffer, and the like. In the case of saline, a 0.9% saline solution may be employed. In the case of acetate, phosphate, citrate, acetate and the like, a 50 mM solution may be employed.

The compounds and pharmaceutical compositions of this invention may be formulated for and administered by means of an injection, typically a deep intramuscular injection, such as in the gluteal or deltoid muscle, of a time release or depot injectable formulation. Such time release or injectable depot forms may be made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations may also be prepared by entrapping the compound in liposomes or microemulsions that are compatible with body tissues. In one embodiment, a compound or pharmaceutical composition of this invention is formulated with a PEG, such as poly(ethylene glycol) 3350, and optionally one or more additional excipients and preservatives, including but not limited to excipients such as salts, polysorbate 80, sodium hydroxide or hydrochloric acid to adjust pH, and the like. In another embodiment, a compound or pharmaceutical composition of this invention is formulated with glyceryl monostearate or glyceryl distearate, optional with one or more pharmaceutically acceptable waxes. In another embodiment a compound or pharmaceutical composition of this invention is formulated with a poly(orthoester), which may be an auto-catalyzed poly(orthoester) with any of a variable percentage of lactic acid in the polymeric backbone, and optionally one or more additional excipients. In one embodiment poly (D,L-lactide-co-glycolide) polymer (PLGA polymer) is employed, preferably a PLGA polymer with a hydrophilic end group, such as PLGA RG502H from Boehringer Ingelheim, Inc. (Ingelheim, Germany). Such formulations may be made, for example, by combining a compound of this invention in a suitable solvent, such as methanol, with a solution of PLGA in methylene chloride, and adding thereto a continuous phase solution of polyvinyl alcohol under suitable mixing conditions in a reactor. In general, any of a number of injectable and biodegradable polymers may be employed in a time release or depot injectable formulation. The formulation may be such that an injection is required on a daily, weekly, monthly or other periodic basis, depending on the concentration and amount of construct, the biodegradation rate of the polymer, and other factors known to those of skill in the art.

5.1 Pharmaceutically Effective Amount

In general, the actual quantity of compound of this invention administered to a patient will vary between fairly wide ranges depending upon the mode of administration, the formulation used, and the response desired. The dosage for treatment is administration, by any of the foregoing means or any other means known in the art, of an amount sufficient to bring about the desired effect. This may readily be determined by one of ordinary skill in the art through means such as pharmacokinetic studies, plasma half-life studies, dose escalation studies, and the like. Thus a pharmaceutically effective amount includes an amount of a compound or pharmaceutical composition of this invention that is sufficient to induce the desired effect.

In general, the compounds of this invention are highly active, with dose responses as low as 0.001 µg/kg, generally with optimal or peak dose responses between about 0.01 µg/kg and 25 µg/kg, depending on the specific compound and the route of administration. For example, the compound can be administered at 0.001, 0.005, 0.01, 0.05, 0.1, 0.5, 1, 5, 10, or 50 µg/kg body weight, depending on specific compound selected, the desired response, the route of administration, the formulation and other factors known to those of skill in the art. Conventional dose response studies and other pharmacological means may be employed to determine the optimal dose for a desired effect with a given compound, given formulation and given route of administration.

5.2 Clinical Indications and Applications

In a broad aspect, compounds of this invention may be utilized, therapeutically or prophylactically, for any disorder, condition, disease or syndrome in which inhibition of eEF2 kinase activity, or decrease or limitation of EF2 phosphorylation, is desirable or advantageous.

In one aspect, compounds of this invention are utilized therapeutically or prophylactically in the treatment of any of a variety of cancers, optionally in combination with one or more chemotherapeutic agents. Such cancers include breast, lung, head and neck, bladder and other cancers. In some embodiments, the cancer is associated with a solid tumor. In certain embodiments, the cancer is breast cancer, glioblastoma, lung cancer, cancer of the head and neck, colorectal cancer, bladder cancer, or non-small cell lung cancer. In some embodiments, the present invention provides a method for treating or lessening the severity of one or more disorders selected from squamous cell carcinoma, salivary gland carcinoma, ovarian carcinoma, or pancreatic cancer. In certain embodiments, the present invention provides a method for treating or lessening the severity of neurofibromatosis type I (NF1), neurofibromatosis type II (NF2) Schwann cell neoplasms (e.g. MPNST's), or Schwannomas.

In another aspect, compounds of this invention are utilized therapeutically or prophylactically in the treatment of any of a variety of proliferative diseases, optionally in combination with one or more antiproliferative agents. Such proliferative diseases include myeloproliferative disorders and diseases, such as polycythemia vera, thrombocythemia, myeloid metaplasia with myelofibrosis, hypereosinophilic syndrome, juvenile myelomonocytic leukemia, systemic mast cell disease, and hematopoietic disorders, in particular, acute-myelogenous leukemia (AML), chronic-myelogenous leukemia (CML), acute-promyelocytic leukemia (APL), and acute lymphocytic leukemia (ALL).

In another aspect, compounds of this invention are utilized therapeutically to treat Alzheimer's disease or other neurodegenerative disease, optionally in combination with one or more additional therapeutic agents.

In another aspect, compounds of this invention are utilized therapeutically or prophylactically to prevent, reduce or eliminate the effects of ionizing radiation in a subject who has incurred or is at risk for incurring exposure to ionizing radiation. Such ionizing radiation may be used medically to treat disease, such as with external beam radiation, brachytherapy or systemic radiation therapy. Compounds of this invention may also be employed to treat or prevent injury from the effects of non-medical ionizing radiation, such as environmental and atmospheric radiation whether natural or man-made, radiation caused by nuclear weapons, terrorist attack, war, and so on.

5.2.1 Combination with Chemotherapy Agents

For treatment of a proliferative disease or cancer, a compound of this invention, including a pharmaceutical composition of this invention, may be administered in combination with one or more chemotherapeutic agents. By "administered in combination with" is meant administered in temporal proximity, such that both the compound of this invention and the chemotherapeutic agent are either concurrently pharmacologically active in the patient, or are each pharmacologically active within at least a portion of a defined period of time, such as one day, two days, three days, four days or five days. By way of example, a compound of this invention may be administered three days, two days or one day prior to administration of a chemotherapeutic agent. Alternatively, a compound of this invention may be administered on the same day as a chemotherapeutic agent, or may be administered one day, two days or three days after administration of a chemotherapeutic agent. In one embodiment, a compound of this invention is compounded or formulated with a chemotherapeutic agent, such that the both are co-administered in a single injection, or co-formulated in a single tablet or capsule. In another embodiment, differents routes of administration are utilized, such that a compound of this invention is administered by one route, and a chemotherapeutic agent is administered by another route.

Examples of known chemotherapeutic agents include, but are not limited to, doxorubicin, dexamethasone, vincristine, cyclophosphamide, fluorouracil, topotecan, taxol, interferons, platinum derivatives, taxane (e.g., paclitaxel), vinca alkaloids (e.g., vinblastine), various anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, emetine, trimetrexate, metoprine, cyclosporine, daunorubicin, teniposide, amphotericin, alkylating agents (e.g., chlorambucil), 5-fluorouracil, camptothecin, cisplatin, metronidazole, and imatinib mesylate, sold under the trade name GLEEVEC®, among others. In other embodiments, a compound of this invention is administered in combination with a biologic agent, such as bevacizumab, sold under the trade name AVASTIN®, or panitumumab, sold under the trade name VECTIBIX®.

In certain embodiments, a compound of this invention may be administered in combination with an antiproliferative or chemotherapeutic agent selected from any one or more of abarelix, aldesleukin, alemtuzumab, alitretinoin, allopurinol, altretamine, amifostine, anastrozole, arsenic trioxide, asparaginase, azacitidine, BCG Live, bevacuzimab, fluorouracil, bexarotene, bleomycin, bortezomib, busulfan, calusterone, capecitabine, camptothecin, carboplatin, carmustine, celecoxib, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, erlotinib, estramustine, etoposide phosphate, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, or zoledronic acid.

5.2.2 Combination with Agents for the Treatment of Alzheimer's Disease and Other Neurodegenerative Diseases For treatment of Alzheimer's or other neurodegenerative disease, a compound of this invention, including a pharmaceutical composition of this invention, may be administered in combination with one or more other agents. As with chemotherapeutic agents, by "administered in combination with" is meant administered in temporal proximity, such that both the compound of this invention and the other agent are concurrently pharmacologically active in the patient. Compounds of this invention may administered in combination with any agent for the treatment of Alzheimer's or other neurodegenerative disease, such as donepezil hydrochloride (ARICEPT®) and rivastigmine (Exelon). Compounds of this invention may administered in combination with any agent for the treatment of Parkinson's disease such as L-DOPA/carbidopa, entacapone, ropinrole, pramipexole, bromocriptine, pergolide, trihexephendyl, and amantadine. Compounds of this invention may administered in combination with any agent for the treatment of multiple sclerosis such as beta interferon (e.g., AVONEX®), glatiramer acetate (COPAXONE®), and mitoxantrone. Compounds of this invention may administered in combination with any agent for which treatment with an immunomodulatory or immunosuppressive agents is desired, such as in combination with cyclosporin, tacrolimus, rapamycin, mycophenolate mofetil, interferons, corticosteroids, cyclophophamide, azathioprine, and sulfasalazine, neurotrophic factors such as acetylcholinesterase inhibitors, MAO inhibitors, interferons, anticonvulsants, ion channel blockers, riluzole, and anti-Parkinsonian agents.

5.2.3 Use with Radiation Agents

In general, the compounds of this invention are cytoprotective agents, and prevent, reduce or eliminate the effects of ionizing radiation in a subject who has incurred or is at risk for incurring exposure to ionizing radiation. In one embodiment, a compound of this invention is administered prior to, concomitant with and/or after the exposure to ionizing radiation. In another embodiment, the radiation comprises clinical or non-clinical ionizing radiation which can be anticipated, is planned or is inadvertent. The clinical ionizing radiation includes, by way of example and not limitation, radiation used in clinical settings in diagnostic systems and assays, radiation used for prevention, treatment or amelioration of symptoms of disease or disorder such as cancer (e.g., radiotherapy), among others. The non-clinical ionizing radiation includes, by way of example and not limitation, environmental and atmospheric radiation whether natural or man-made, radiation caused by nuclear weapons, terrorist attack, war, and so on.

In one embodiment, compounds of this invention are intended for either prophylactic or treatment use, or both. Thus a compound of this invention can be used to enhance survival in personnel who are in imminent danger of exposure to life-threatening levels of x-ray or gamma radiation, or alternatively to enhance survival in personnel who have just received life-threatening levels of x-ray or gamma radiation.

In yet another embodiment, subjects may be exposed to ionizing radiation when undergoing therapeutic irradiation for the treatment of proliferative disorders. Such disorders include cancerous and non-cancer proliferative disorders. Compounds of this invention are effective in protecting normal cells during therapeutic irradiation of a broad range of tumor types, including but not limited to the following: breast, prostate, ovarian, lung, colorectal, brain (i.e., glioma) and renal. The compounds of this invention are also effective against leukemic cells, for example. The compounds are useful in protecting normal cells during therapeutic irradiation of abnormal tissues in non-cancer proliferative disorders, including but not limited to hemangiomatosis, secondary progressive multiple sclerosis, chronic progressive myelodegenerative disease, neurofibromatosis, ganglioneuromatosis, keloid formation, Paget's Disease of the bone, fibrocystic disease of the breast, Peyronie's and Duputren's fibrosis, restenosis and cirrhosis, among others.

Therapeutic ionizing radiation may be administered to a subject on any schedule and in any dose consistent with the prescribed course of therapy. Compounds of this invention may be administered far enough in advance of the radiation, whether anticipated, planned or inadvertent, concomitant with exposure to radiation, and/or after exposure to radiation such that the compound is able to reach the normal cells of the subject in sufficient concentration to exert a radioprotective or mitigative effect on the normal cells. By way of example, a compound of this invention may be administered as much as about 24 hours prior to or after the administration of the radiation. In one embodiment, a compound of this invention is administered at least about 6-24 hours before exposure to radiation. In another embodiment, compounds of this invention are administered once at about 24 hours and again at about 15 minutes before the radiation exposure. Alternatively, a compound of this invention could be administered once 24 hours prior to radiation exposure and again at about 48 hours post-radiation. In one embodiment, about a 24 hour period separates administration of a compound of this invention and the therapeutic radiation. In another embodiment, the administration of a compound of this

23 invention and the therapeutic radiation is separated by about 6 to 18 hours.

6. Examples

The following compounds were synthesized using one of the foregoing schemes, or alternatively using one or more variants on one of the foregoing schemes. In the following listings, the chemical naming protocol and structure diagrams employ and rely on the chemical naming features as utilized by the ChemDraw program (available from Cambridgesoft Corp.) or ISIS Draw (MDL Information Systems, Inc.). In particular, the compound names were derived from the structures using the Autonom program as utilized by ChemDraw Ultra or ISIS Draw. In the structure diagrams, hydrogens are assumed and not disclosed, except as otherwise shown.

Example 1

The following compounds were synthesized using the general methods described above. In the table below, $IC_{50}$ values are in $\mu M$ and are the average of two to four separate experimental measurements, each consisting in turn of the average of three replicates. $IC_{50}$ values were calculated using the methods as described in Example 2. MW was determined by mass spectroscopy analysis, and is expressed as M+1.

| Compound | Number | MW | $IC_{50}$ |
|---|---|---|---|
| 3-Amino-4-(5-chloro-furan-2-yl)-8-(5-chloro-furan-2-ylmethylene)-6,6-dimethyl-5,6,7,8-tetrahydro-thieno[2,3-b]quinoline-2-carboxylic acid amide | 1 | 488 | 2.7 |
| 3-Amino-4-(5-chloro-furan-2-yl)-6,6-dimethyl-5,6,7,8-tetrahydro-thieno[2,3-b]quinoline-2-carboxylic acid amide | 2 | 375.5 | 1.1 |
| 3-Amino-4-(5-chloro-furan-2-yl)-8-(5-chloro-furan-2-ylmethylene)-6-phenyl-5,6,7,8-tetrahydro-thieno[2,3-b]quinoline-2-carboxylic acid amide | 3 | 535 | 10000 |

| Compound | Number | MW | IC$_{50}$ |
|---|---|---|---|
| 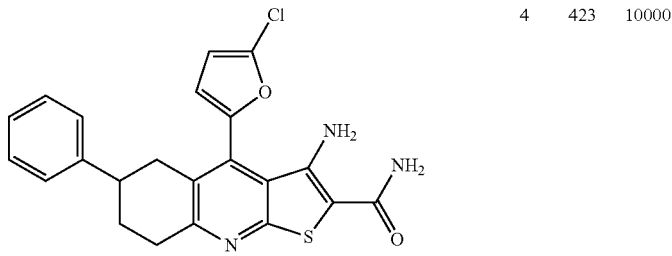  3-Amino-4-(5-chloro-furan-2-yl)-6-phenyl-5,6,7,8-tetrahydro-thieno[2,3-b]quinoline-2-carboxylic acid amide | 4 | 423 | 10000 |
| 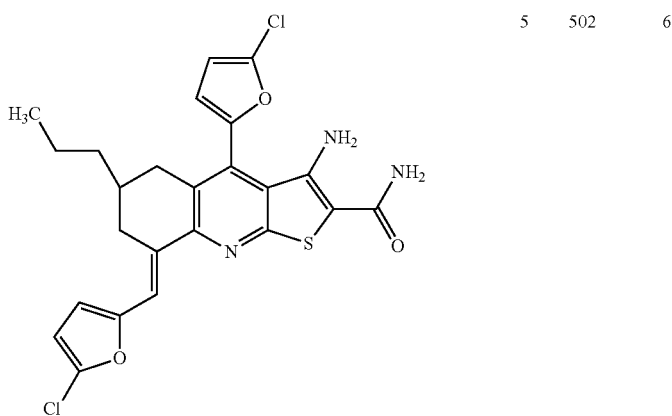  3-Amino-4-(5-chloro-furan-2-yl)-8-(5-chloro-furan-2-ylmethylene)-6-propyl-5,6,7,8-tetrahydro-thieno[2,3-b]quinoline-2-carboxylic acid amide | 5 | 502 | 6 |
| 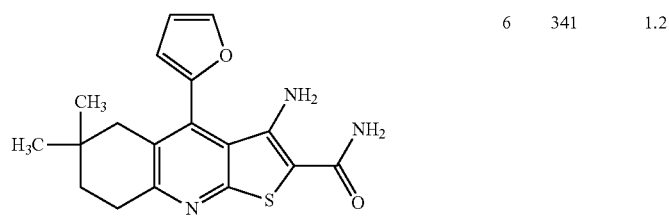  3-Amino-4-furan-2-yl-6,6-dimethyl-5,6,7,8-tetrahydro-thieno[2,3-b]quinoline-2-carboxylic acid amide | 6 | 341 | 1.2 |
| 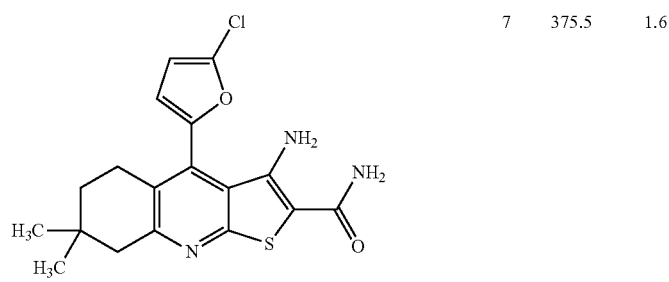  3-Amino-4-(5-chloro-furan-2-yl)-7,7-dimethyl-5,6,7,8-tetrahydro-thieno[2,3-b]quinoline-2-carboxylic acid amide | 7 | 375.5 | 1.6 |

-continued

| Compound | Number | MW | IC$_{50}$ |
|---|---|---|---|
| 3-Amino-4-(5-chloro-furan-2-yl)-8,8-dimethyl-5,6,7,8-tetrahydro-thieno[2,3-b]quinoline-2-carboxylic acid amide | 8 | 375.5 | 4.7 |
| 3-Amino-4-(5-chloro-furan-2-yl)-7,7-dimethyl-6,7-dihydro-5H-1-thia-8-aza-s-indacene-2-carboxylic acid amide | 9 | 361.5 | 2.4 |
| 3-Amino-4-furan-2-yl-7,7-dimethyl-5,6,7,8-tetrahydro-thieno[2,3-b]quinoline-2-carboxylic acid amide | 10 | 341 | 1 |
| 3-Amino-4-(3,4-dichloro-phenyl)-7,7-dimethyl-5,6,7,8-tetrahydro-thieno[2,3-b]quinoline-2-carboxylic acid amide | 11 | 420 | 23 |

-continued

| Compound | Number | MW | IC$_{50}$ |
|---|---|---|---|
| 3-Amino-4-(5-chloro-furan-2-yl)-5,7,7-trimethyl-5,6,7,8-tetrahydro-thieno[2,3-b]quinoline-2-carboxylic acid amide | 12 | 389 | 5 |
| 3-Amino-4-(5-chloro-furan-2-yl)-8-phenyl-5,6,7,8-tetrahydro-thieno[2,3-b]quinoline-2-carboxylic acid amide | 13 | 423 | 31 |
| 3-Amino-8-(3-chloro-2-fluoro-benzylidene)-4-(3-chloro-2-fluoro-phenyl)-6,6-dimethyl-5,6,7,8-tetrahydro-thieno[2,3-b]quinoline-2-carboxylic acid amide | 14 | 543 | 5022 |
| 3-Amino-4-furan-2-yl-7,7-dimethyl-6,7-dihydro-5H-1-thia-8-aza-s-indacene-2-carboxylic acid amide | 15 | 327 | 2.5 |

-continued

| Compound | Number | MW | IC$_{50}$ |
|---|---|---|---|
| 3-Amino-4-furan-2-yl-5,7,7-trimethyl-5,6,7,8-tetrahydro-thieno[2,3-b]quinoline-2-carboxylic acid amide | 16 | 355 | 4.6 |
| 3-Amino-4-furan-3-yl-7,7-dimethyl-6,7-dihydro-5H-1-thia-8-aza-s-indacene-2-carboxylic acid amide | 17 | 327 | 1.1 |
| 3-Amino-7,7-dimethyl-4-thiophen-3-yl-6,7-dihydro-5H-1-thia-8-aza-s-indacene-2-carboxylic acid amide | 18 | 343 | 0.9 |
| 3-Amino-4-cyclopropyl-7,7-dimethyl-6,7-dihydro-5H-1-thia-8-aza-s-indacene-2-carboxylic acid amide | 19 | 301 | 1.1 |
| 3-Amino-6,6-dimethyl-4-thiophen-3-yl-5,6,7,8-tetrahydro-thieno[2,3-b]quinoline-2-carboxylic acid amide | 20 | 357 | 2.2 |

-continued

| Compound | Number | MW | IC$_{50}$ |
|---|---|---|---|
| 3-Amino-4-furan-3-yl-6,6-dimethyl-5,6,7,8-tetrahydro-thieno[2,3-b]quinoline-2-carboxylic acid amide | 21 | 341 | 2 |
| 3-Amino-4-furan-3-yl-8-furan-3-ylmethylene-6,6-dimethyl-5,6,7,8-tetrahydro-thieno[2,3-b]quinoline-2-carboxylic acid amide | 22 | 419 | 6 |
| 3-Amino-7,7-dimethyl-4-thiazol-2-yl-6,7-dihydro-5H-1-thia-8-aza-s-indacene-2-carboxylic acid amide | 23 | 344 | 2 |
| 3-Amino-4-(5-chloro-thiophen-2-yl)-7,7-dimethyl-6,7-dihydro-5H-1-thia-8-aza-s-indacene-2-carboxylic acid amide | 24 | 377 | 1.4 |

-continued

| Compound | Number | MW | IC$_{50}$ |
|---|---|---|---|
| 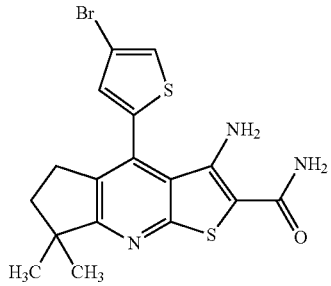 [SMILES: CC1(C)CCc2c1nc1sc(C(N)=O)c(N)c1c2-c1cc(Br)cs1] 3-Amino-4-(4-bromo-thiophen-2-yl)-7,7-dimethyl-6,7-dihydro-5H-1-thia-8-aza-s-indacene-2-carboxylic acid amide | 25 | 423 | 0.8 |
| 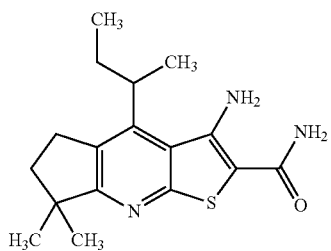 [SMILES: CCC(C)c1c2c(nc3sc(C(N)=O)c(N)c13)C(C)(C)CC2] 3-Amino-4-sec-butyl-7,7-dimethyl-6,7-dihydro-5H-1-thia-8-aza-s-indacene-2-carboxylic acid amide | 26 | 317 | 1 |
| 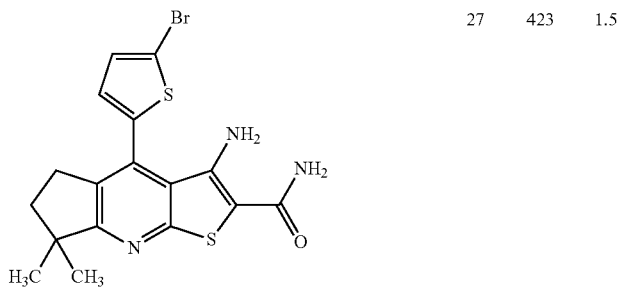 3-Amino-4-(5-bromo-thiophen-2-yl)-7,7-dimethyl-6,7-dihydro-5H-1-thia-8-aza-s-indacene-2-carboxylic acid amide | 27 | 423 | 1.5 |
| 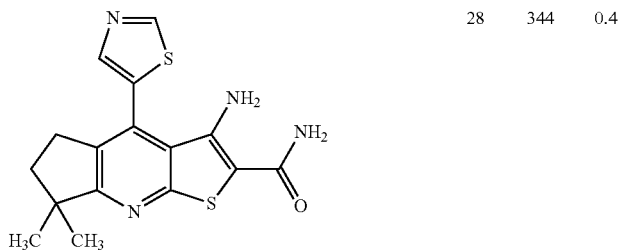 3-Amino-7,7-dimethyl-4-thiazol-5-yl-6,7-dihydro-5H-1-thia-8-aza-s-indacene-2-carboxylic acid amide | 28 | 344 | 0.4 |

-continued

| Compound | Number | MW | IC$_{50}$ |
|---|---|---|---|
| 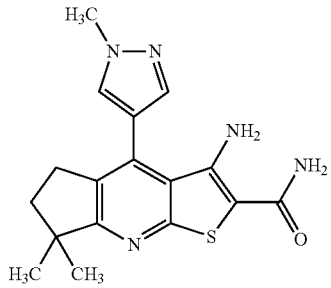 [SMILES: Cn1cc(-c2c3c(nc4sc(C(N)=O)c(N)c24)C(C)(C)CC3)cn1] 3-Amino-7,7-dimethyl-4-(1-methyl-1H-pyrazol-4-yl)-6,7-dihydro-5H-1-thia-8-aza-s-indacene-2-carboxylic acid amide | 29 | 341 | 0.7 |
| 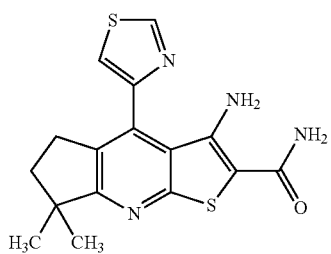 [SMILES: CC1(C)CCc2c1nc1sc(C(N)=O)c(N)c1c2-c1cscn1] 3-Amino-7,7-dimethyl-4-thiazol-4-yl-6,7-dihydro-5H-1-thia-8-aza-s-indacene-2-carboxylic acid amide | 30 | 344 | 3.4 |
| 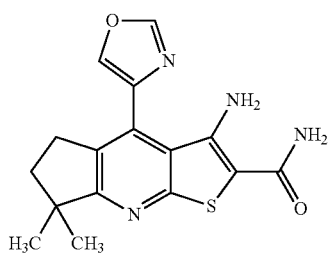 3-Amino-7,7-dimethyl-4-oxazol-4-yl-6,7-dihydro-5H-1-thia-8-aza-s-indacene-2-carboxylic acid amide | 31 | 328 | 3.5 |
| 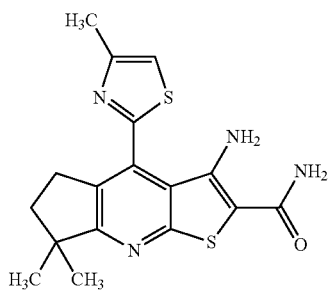 3-Amino-7,7-dimethyl-4-(4-methyl-thiazol-2-yl)-6,7-dihydro-5H-1-thia-8-aza-s-indacene-2-carboxylic acid amide | 32 | 358 | 3.8 |

-continued

| Compound | Number | MW | IC$_{50}$ |
|---|---|---|---|
| 3-Amino-6,6-dimethyl-4-thiazol-5-yl-5,6,7,8-tetrahydro-thieno[2,3-b]quinoline-2-carboxylic acid amide | 33 | 358 | 1.1 |
| 3-Amino-4-(3-bromo-thiophen-2-yl)-7,7-dimethyl-6,7-dihydro-5H-1-thia-8-aza-s-indacene-2-carboxylic acid amide | 34 | 422 | 0.8 |
| 3-Amino-7,7-dimethyl-4-thiazol-5-yl-5,6,7,8-tetrahydro-thieno[2,3-b]quinoline-2-carboxylic acid amide | 35 | 358 | 0.4 |
| 3-Amino-5,7,7-trimethyl-4-thiazol-5-yl-5,6,7,8-tetrahydro-thieno[2,3-b]quinoline-2-carboxylic acid amide | 36 | 372 | 0.4 |
| 3-Amino-4-(4-bromo-furan-2-yl)-8,8-dimethyl-5,6,7,8-tetrahydro-thieno[2,3-b]quinoline-2-carboxylic acid amide | 37 | 420 | 0.9 |

-continued

| Compound | Number | MW | IC$_{50}$ |
|---|---|---|---|
| 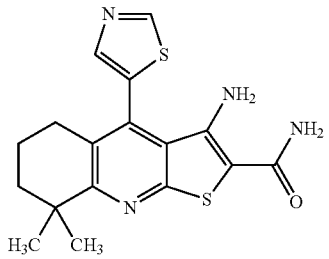 [SMILES: CC1(C)CCCc2c1nc1sc(C(N)=O)c(N)c1c2-c1cncs1]<br>3-Amino-8,8-dimethyl-4-thiazol-5-yl-5,6,7,8-tetrahydro-thieno[2,3-b]quinoline-2-carboxylic acid amide | 38 | 358 | 0.3 |
| 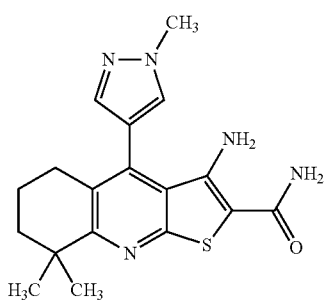 [SMILES: Cn1cc(-c2c3c(nc4sc(C(N)=O)c(N)c24)C(C)(C)CCC3)cn1]<br>3-Amino-8,8-dimethyl-4-(1-methyl-1H-pyrazol-4-yl)-5,6,7,8-tetrahydro-thieno[2,3-b]quinoline-2-carboxylic acid amide | 39 | 355 | 1.4 |
| 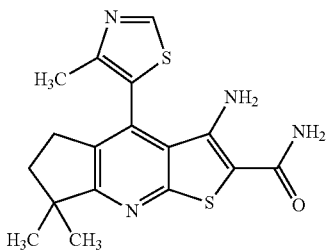 [SMILES: Cc1ncsc1-c1c2c(nc3sc(C(N)=O)c(N)c13)C(C)(C)CC2]<br>3-Amino-7,7-dimethyl-4-(4-methyl-thiazol-5-yl)-6,7-dihydro-5H-1-thia-8-aza-s-indacene-2-carboxylic acid amide | 40 | 358 | 0.4 |
| 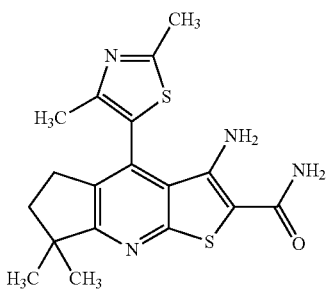 [SMILES: Cc1nc(C)c(-c2c3c(nc4sc(C(N)=O)c(N)c24)C(C)(C)CC3)s1]<br>3-Amino-4-(2,4-dimethyl-thiazol-5-yl)-7,7-dimethyl-6,7-dihydro-5H-1-thia-8-aza-s-indacene-2-carboxylic acid amide | 41 | 372 | 0.5 |

-continued

| Compound | Number | MW | IC$_{50}$ |
|---|---|---|---|
| (structure) | 42 | 384 | 3.1 |
| (structure) | 43 | 342 | 0.9 |

Example 2

To determine the IC$_{50}$ of compounds of the invention, recombinant eEF2K was diluted in an assay buffer in the presence of calmodulin, a calcium-binding messenger protein expressed in eukaryotic cells, and incubated with peptide substrate Ac-RKKYKFNEDTERRRFL in the presence of Adenosine-5'-triphosphate (ATP) and the test compound. The peptide substrate is efficiently and specifically phosphorylated by eEF2K at a single substrate concentration of 100 μM. Using this peptide, eEF2K activity can be quantitatively determined using a Kinase-Glo® luminescent kinase assay kit (Promega) that measures ATP consumption by EF2K during phosphorylation of the substrate. ATP conversion was recorded using Perkin-Elmer Victor Luminometer. Data was plotted using GraphPad software and IC$_{50}$ was calculated using 3-parameter sigmoidal curve fit. FIG. 1 shows the dose-response curve of Compound 35 calculated using this method.

Example 3

Figure 2:
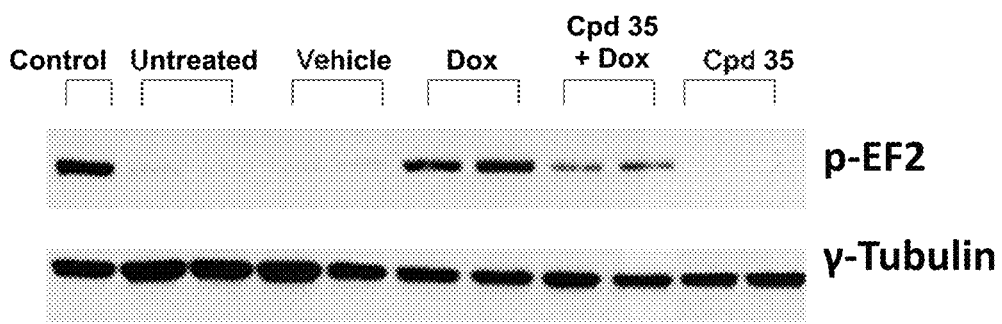
FIG. 2 is a Western blot image of phosphorylation of EF2 to evaluate the efficiency of eEF2K inhibition in mouse embryonic fibroblasts in responses to doxorubicin (Dox) with and without Compound 35, with gamma-tubulin serving as loading control.

Phosphorylation of EF2 was employed to evaluate the efficiency of eEF2K inhibition. Western blotting with a phospho-specific anti-eEF2K antibody (Cell Signaling) was used to demonstrate that compounds of the invention can partially inhibit phosphorylation of EF2 in wild type mouse embryonic fibroblasts (MEFs) in response to doxorubicin. FIG. 2 depicts a Western blot analysis of phosphorylated EF2 treated with 2 μM doxorubicin and 2 μM of Compound 35. Tubulin served as a loading control.

Example 4

Figure 3:
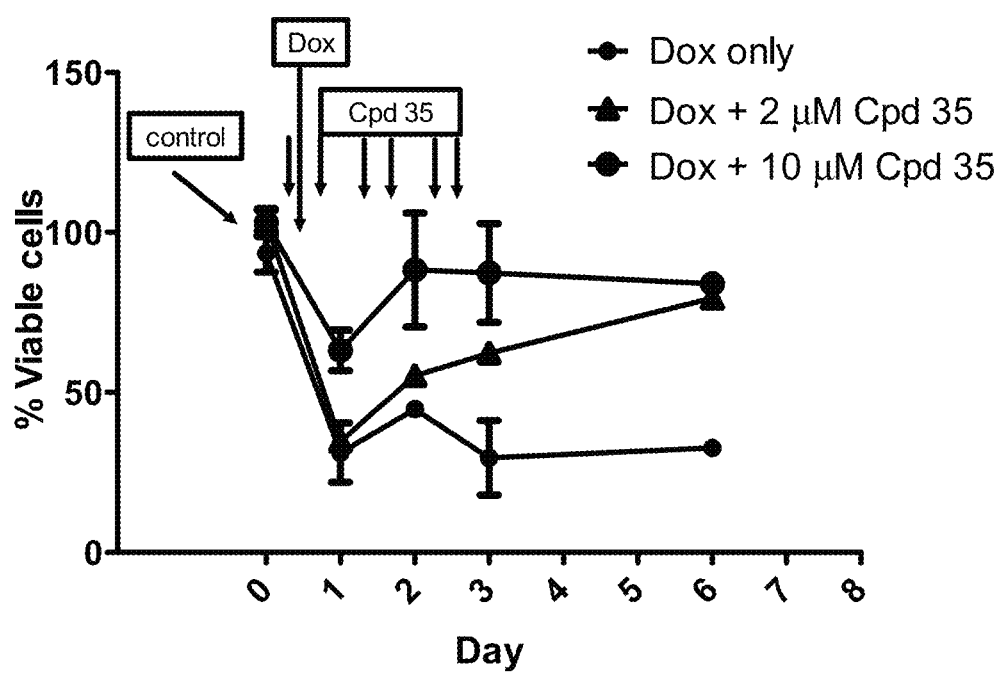
FIG. 3 is a plot of doxorubicin-induced apoptosis in rat embryonic myocardium cells with and without two different concentrations of Compound 35.

Compound 35 was tested on doxorubicin-induced apoptosis in the rat embryonic myocardium cell line H9C2 (ATCC No. CRL-1446). The cells were plated into 48-well plates at $0.2 \times 10^5$ cells per well and allowed to attach overnight. The cells were then exposed to 0.4 μM doxorubicin for 24 hours, with or without 2 μM or 10 μM of Compound 35 twice daily for 72 hours. Cell viability was measured on days 1, 2, 3, and 6 using the Promega CellTiter-Glo® Luminescent Cell Viability Assay. As shown in FIG. 3, in the control arm, exposure to 0.4 μM doxorubicin for 24 hours resulted in 65% cell death. Remaining viable cells failed to proliferate even after doxorubicin was removed after 24 hours. In the Compound 35 arms, a robust, dose-dependent protection of H9C2 cells from the toxicity induced by 0.4 μM doxorubicin was observed. Following 24 hours exposure to doxorubicin, cells treated with 10 μM or 2 μM Compound 35 recovered to 85% of original density by day 2 or day 6, respectively.

Example 5

Figure 4:
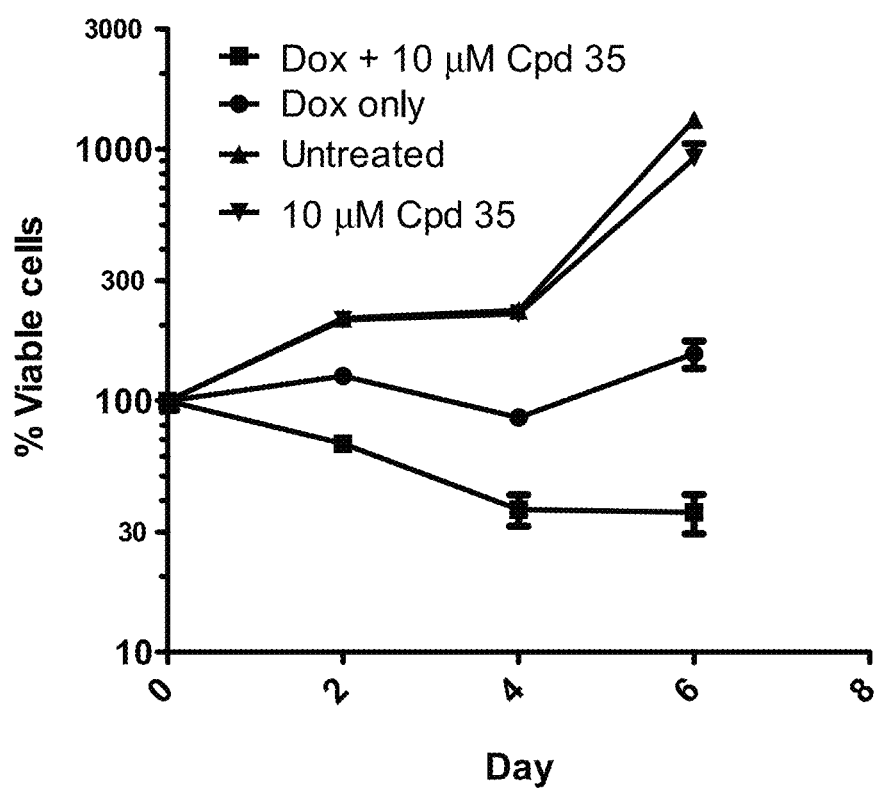
FIG. 4 is a plot of cytoprotective activity of eEf2K inhibition in a breast cancer cell line by Compound 35 with and without doxorubicin (Dox).

The potentiation of doxorubicin effect of eEF2K inhibition by Compound 35 in combination with doxorubicin was evaluated. The breast cancer cell line MDA-MB-231 (ATCC No. HTB-26) was incubated with 0.4 μM doxorubicin for 24 hours, with both a negative control (untreated) group and a group receiving only 10 μM Compound 35 but not doxorubicin. One doxorubicin group was treated with 10 μM of Compound 35 twice daily for 72 hours. Cell viability was measured on days 0, 2, 4, and 6 using the Promega CellTiter-Glo® Luminescent Cell Viability Assay. As shown in FIG. 4, in both the negative control (untreated) and 10 μM Compound 35 without doxorubicin arms, the percent of viable cells increased substantially by day 6. The percent of viable cells in the 0.4 μM doxorubicin arm increased slightly by day 6. However, the percent of viable cells in the arm receiving 0.4 μM doxorubicin for 24 hours and 10 μM of Compound 35 twice daily for 72 hours showed a significant decrease in the percent of viable cells at days 2, 4 and 6, suggesting potentiation of doxorubicin-induced toxicity.

Example 6

Figure 5A:
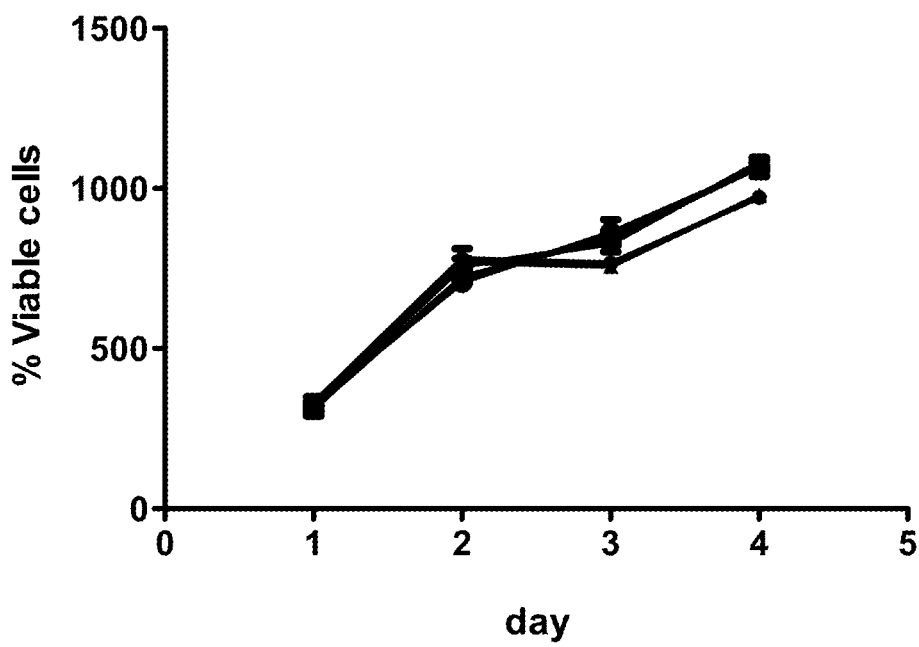
FIG. 5A is a plot of growth of human osteosarcoma cells under normal conditions with no treatment, vehicle and Compound 35.
Figure 5B:
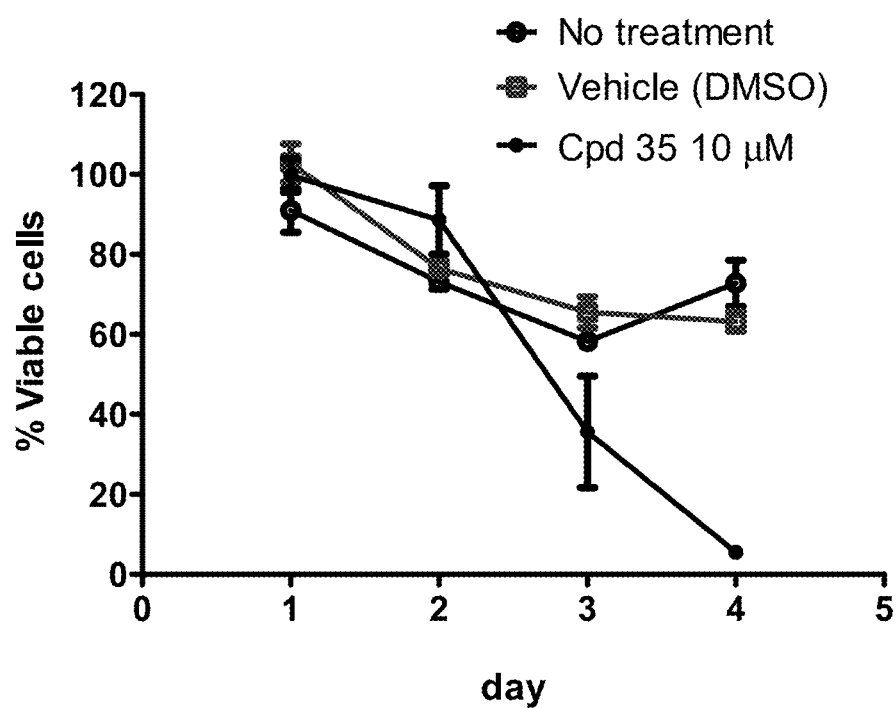
FIG. 5B is a plot of growth of human osteosarcoma cells under nutrient deprivation conditions with no treatment, vehicle and Compound 35.

The effect of eEF2K inhibition on the malignant human bone osteosarcoma cancer cell line MG63 (ATCC No. CRL-1427) was evaluated under both normal conditions and during nutrient deprivation. Cells were plated into 48-well plates at $0.2 \times 10^5$ cells per well and allowed to attach overnight. One group of cells were grown under normal conditions (advanced MEM/glutamine/10% FBS) and the other group of cells were switched to conditions of nutrient deprivation (HBSS/22 mM HEPES) twenty-four hours after plating. Each group was divided into three subsets: cells receiving no treatment; cells receiving vehicle (DMSO) and cells receiving 10 μM of Compound 35. Cell viability was measured on days 1, 2, 3, and 4 using Promega CellTiter-Glo® Luminescent Cell Viability Assay, with viability normalized to day 0. As shown in FIG. 5A, the group of MG63 cells grown under normal conditions showed significant growth for all subsets. The group of MG63 cells grown under nutrient deprivation conditions, as shown in FIG. 5B, showed substantially similar decreases in the percent viable cells in the no treatment and vehicle subsets, and substantially greater decrease, such that less than 10% of cells were viable by day 6 in the 10 μM of Compound 35 subset.

Example 7

In pharmacokinetic studies, intravenous administration of 1 mg/kg of Compound 35 in male CD-1 mice showed a half-life at 34 minutes and $C_{max}$ of 356 ng/mL at five minutes.

Example 8

Compound 35 was formulated for injection as a solution consisting of 20% DMSO, 45% castor oil and 35% ethanol.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above, and of the corresponding application(s), are hereby incorporated by reference.

What is claimed is:

1. A compound of the formula

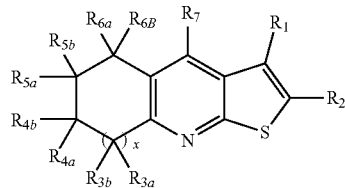

wherein:
$R_1$ is —$N(R_8)_2$;
$R_2$ is —$C(=O)$—$N(R_8)_2$;
$R_{3a}$ and $R_{3b}$, if x is 1, are
each H, or
each independently $C_{1-3}$ linear or branched alkyl, optionally together forming cycloalkyl, or one of $R_{3a}$ or $R_{3b}$ is H and the other is $C_{1-3}$ linear alkyl forming a cycloalkyl through one of $R_{5a}$, $R_{5b}$, $R_{6a}$ or $R_{6b}$,
$R_{4a}$ and $R_{4b}$ are
each H, or
each independently $C_{1-3}$ linear or branched alkyl, optionally together forming cycloalkyl, or
one of $R_{4a}$ or $R_{4b}$ is $C_{1-3}$ linear or branched alkyl and the other is H, or one of $R_{4a}$ or $R_{4b}$ is H and the other is $C_{1-3}$ linear alkyl forming a cycloalkyl through one of $R_{6a}$ or $R_{6b}$, $R_{5a}$ and $R_{5b}$ are
each H, or
each independently $C_{1-3}$ linear or branched alkyl, optionally together forming cycloalkyl, or
if x is 1, one of $R_{5a}$ or $R_{5b}$ forms a cycloalkyl with $R_{3a}$ or $R_{3b}$ and the other is H;
$R_{6a}$ and $R_{6b}$ are
each H, or
each independently $C_{1-3}$ linear or branched alkyl, optionally together forming cycloalkyl, or
one of $R_{6a}$ or $R_{6b}$ forms a cycloalkyl with one of $R_{3a}$ or $R_{3b}$ if x is 1, or if x is 0 or 1, with $R_{4a}$ or $R_{4b}$ and the other is H;
on the proviso that
each member of at least one of the pairs $R_{3a}$ and $R_{3b}$, $R_{4a}$ and $R_{4b}$, $R_{5a}$ and $R_{5b}$, or $R_{6a}$ and $R_{6b}$ is independently $C_{1-3}$ linear or branched alkyl, optionally together forming cycloalkyl, or
alternatively if x is 1 then one of $R_{3a}$ or $R_{3b}$ is a $C_{1-3}$ linear alkyl forming a cycloalkyl with one of $R_{5a}$, $R_{5b}$, $R_{6a}$ or $R_{6b}$ or one of $R_{4a}$ or $R_{4b}$ is a $C_{1-3}$ linear alkyl forming a cycloalkyl with one $R_{6a}$ or $R_{6b}$, or
alternatively if x is 0 then one of $R_{4a}$ or $R_{4b}$ is a $C_{1-3}$ linear alkyl forming a cycloalkyl with one $R_{6a}$ or $R_{6b}$;
$R_7$ is thiozolyl, such ring optionally substituted with one or two ring substituents selected from the group consisting of halogen and $C_1$ to $C_4$ linear, branched or cyclic alkyl;
$R_8$ in each instance is independently H or a $C_1$ to $C_4$ linear, branched or cyclic alkyl chain; and
x is 0 or 1.

2. The compound of claim 1, wherein each member of one of the pairs $R_{3a}$ and $R_{3b}$, $R_{4a}$ and $R_{4b}$, $R_{5a}$ and $R_{5b}$, and $R_{6a}$ and $R_{6b}$ is independently $C_{1-3}$ linear or branched alkyl, optionally together forming cycloalkyl, and each member of the remaining pairs $R_{3a}$ and $R_{3b}$, $R_{4a}$ and $R_{4b}$, $R_{5a}$ and $R_{5b}$, and $R_{6a}$ and $R_{6b}$ are H.

3. The compound of claim 1, wherein each member of one of the pairs $R_{3a}$ and $R_{3b}$, $R_{4a}$ and $R_{4b}$, $R_{5a}$ and $R_{5b}$, and $R_{6a}$ and $R_{6b}$ is independently $C_{1-3}$ linear or branched alkyl, optionally together forming cycloalkyl, one of the remaining pairs $R_{3a}$ and $R_{3b}$, $R_{4a}$ and $R_{4b}$, $R_{5a}$ and $R_{5b}$, and $R_{6a}$ and $R_{6b}$ contains a member that is H and a member that is $C_{1-3}$ linear or branched alkyl, and each member of the remaining pairs $R_{3a}$ and $R_{3b}$, $R_{4a}$ and $R_{4b}$, $R_{5a}$ and $R_{5b}$, and $R_{6a}$ and $R_{6b}$ are H.

4. The compound of claim 2 which is of the formula

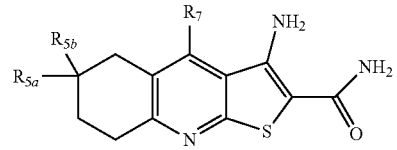

wherein each of $R_{5a}$ and $R_{5b}$ is independently $C_{1-3}$ linear or branched alkyl, optionally together forming cycloalkyl.

5. The compound of claim 2 which is of the formula

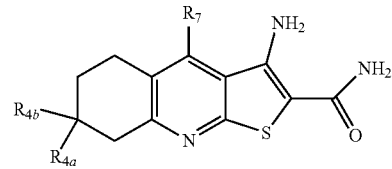

wherein each of $R_{4a}$ and $R_{4b}$ is independently $C_{1-3}$ linear or branched alkyl, optionally together forming cycloalkyl.

6. The compound of claim 2 which is of the formula

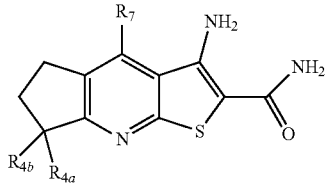

wherein each of $R_{4a}$ and $R_{4b}$ is independently $C_{1-3}$ linear or branched alkyl, optionally together forming cycloalkyl.

7. The compound of claim 3 which is of the formula

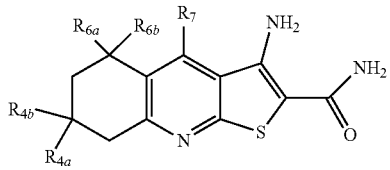

wherein
each of $R_{4a}$ and $R_{4b}$ is independently $C_{1-3}$ linear or branched alkyl, optionally together forming cycloalkyl; and
one of $R_{6a}$ or $R_{6b}$ is $C_{1-3}$ linear or branched alkyl and the other is H.

8. The compound of claim 1 which is of the formula

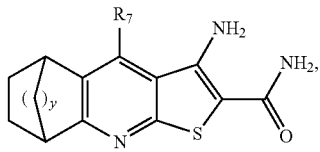

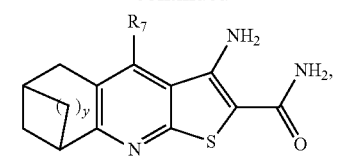

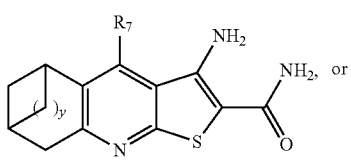

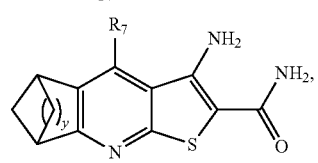

wherein y is 1 to 3.

9. The compound of claim 5 which is of the formula

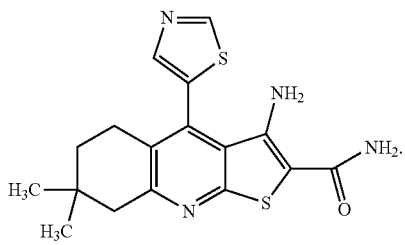 [SMILES: CC1(C)CCc2c(nc3sc(C(N)=O)c(N)c3c2-c2cncs2)C1]

10. A pharmaceutical composition comprising the compound of claim 1 and a pharmaceutically acceptable carrier.

11. A pharmaceutical composition comprising the compound of claim 9 and a pharmaceutically acceptable carrier.

* * * * *